United States Patent
Azuma et al.

(10) Patent No.: US 11,435,320 B2
(45) Date of Patent: Sep. 6, 2022

(54) PLANT MONITORING APPARATUS, PLANT MONITORING METHOD, AND COMPUTER-READABLE RECORDING MEDIUM

(71) Applicant: NEC CORPORATION, Tokyo (JP)

(72) Inventors: Tan Azuma, Tokyo (JP); Yusuke Kikuchi, Tokyo (JP); Kousuke Ishida, Tokyo (JP); Shunsuke Akimoto, Tokyo (JP); Kenichiro Fujiyama, Tokyo (JP); Shinji Oominato, Tokyo (JP)

(73) Assignee: NEC CORPORATION, Tokyo (JP)

( * ) Notice: Subject to any disclaimer, the term of this patent is extended or adjusted under 35 U.S.C. 154(b) by 209 days.

(21) Appl. No.: 16/817,906

(22) Filed: Mar. 13, 2020

(65) Prior Publication Data
US 2020/0292502 A1 Sep. 17, 2020

(30) Foreign Application Priority Data
Mar. 14, 2019 (JP) .............................. JP2019-046893

(51) Int. Cl.
*G01N 29/12* (2006.01)
*G01N 29/44* (2006.01)
(Continued)

(52) U.S. Cl.
CPC ......... *G01N 29/12* (2013.01); *G01N 29/4436* (2013.01); *G01N 33/0098* (2013.01); *A01G 7/00* (2013.01)

(58) Field of Classification Search
CPC ............... G01N 29/12; G01N 29/4436; G01N 33/0098; A01G 7/00
(Continued)

(56) References Cited

U.S. PATENT DOCUMENTS 6,347,551 B1 * 2/2002 Turpening ........... G01N 29/223
73/598
2004/0095154 A1 * 5/2004 Lundstrom ......... G01N 33/246
324/694
(Continued)

FOREIGN PATENT DOCUMENTS

| JP | 2015-112083 A | 6/2015 |
| JP | 2015-202056 A | 11/2015 |

(Continued)

OTHER PUBLICATIONS

Communication dated Apr. 14, 2020, from the Japanese Patent Office in Application No. 2019-046893.
(Continued)

*Primary Examiner* — Alexander A Mercado
*Assistant Examiner* — Monica S Young
(74) *Attorney, Agent, or Firm* — Sughrue Mion, PLLC

(57) ABSTRACT

A plant monitoring apparatus 1 includes: an extraction unit 2 that extracts a feature amount in a frequency response of vibration of a target plant with use of the vibration; a calculation unit 3 that calculates a change that indicates growth of the plant, based on the extracted feature amount and a reference feature amount that corresponds to a reference state of the plant; and an estimation unit 4 that estimates a state of the plant by, with use of the calculated change, referencing state information in which changes of the feature amount from the reference feature amount corresponding to growth of the plant are associated with states of the plant.

6 Claims, 19 Drawing Sheets

(51) Int. Cl.
*G01N 33/00* (2006.01)
*A01G 7/00* (2006.01)

(58) Field of Classification Search
USPC .......................................................... 73/579
See application file for complete search history.

(56) References Cited

U.S. PATENT DOCUMENTS

| | | | | |
|---|---|---|---|---|
| 2011/0288689 | A1* | 11/2011 | Kageyama | G01N 29/07 73/599 |
| 2012/0019382 | A1* | 1/2012 | Kohler | A01G 7/00 340/10.1 |
| 2019/0200535 | A1* | 7/2019 | Regan | B64C 39/024 |
| 2020/0271625 | A1* | 8/2020 | Takemoto | G01N 29/12 |
| 2020/0408719 | A1* | 12/2020 | Inamoto | G01G 3/16 |

FOREIGN PATENT DOCUMENTS

| | | |
|---|---|---|
| JP | 2016/017150 A1 | 4/2017 |
| JP | 2019-154398 A | 9/2019 |
| WO | 2019/031181 A1 | 2/2019 |

OTHER PUBLICATIONS

Communication dated Oct. 13, 2020, from Japanese Patent Office in corresponding JP Application No. 2019-046893.

* cited by examiner

Fig. 4

| PORTION | CHANGE PARAMETER | | CHANGE INFORMATION ||||||| 
|---|---|---|---|---|---|---|---|---|---|
| | | | fc1 CHANGE | fc1 Q FACTOR CHANGE | fc2 CHANGE | fc2 Q FACTOR CHANGE | fc3 CHANGE | fc3 Q FACTOR CHANGE | ... |
| STEM | DIAMETER | +10.0[mm] | +0.1[Hz] | 0 | 0 | 0 | 0 | 0 | ... |
| | | ⋮ | ⋮ | ⋮ | ⋮ | ⋮ | ⋮ | ⋮ | ... |
| | HEIGHT | +10.0[mm] | 0 | 0 | 0 | 0 | +0.3[Hz] | 0 | ... |
| | | ⋮ | ⋮ | ⋮ | ⋮ | ⋮ | ⋮ | ⋮ | ... |
| | INCLINATION | 0 | 0 | 0 | 0 | 0 | 0 | 0 | ... |
| | | ⋮ | ⋮ | ⋮ | ⋮ | ⋮ | ⋮ | ⋮ | ... |
| ⋮ | ⋮ | ⋮ | ⋮ | ⋮ | ⋮ | ⋮ | ⋮ | ⋮ | ... |

| fc1 CHANGE | fc1 Q FACTOR CHANGE | fc2 CHANGE | fc2 Q FACTOR CHANGE | fc3 CHANGE | fc3 Q FACTOR CHANGE | ... |
|---|---|---|---|---|---|---|
| +0.11[Hz] | 0 | 0 | 0 | 0 | 0 | ... |

| PORTION | CHANGE PARAMETER | | CHANGE INFORMATION | | | | | | |
|---|---|---|---|---|---|---|---|---|---|
| | | | fc1 CHANGE | fc1 Q FACTOR CHANGE | fc2 CHANGE | fc2 Q FACTOR CHANGE | fc3 CHANGE | fc3 Q FACTOR CHANGE | ... |
| FIRST BRANCH | DIAMETER | +10.0[mm] | 0 | 0 | +0.3[Hz] | 0 | 0 | 0 | ... |
| | | ⋮ | ⋮ | ⋮ | ⋮ | ⋮ | ⋮ | ⋮ | ... |
| | HEIGHT | +10.0[mm] | 0 | 0 | −0.2[Hz] | 0 | 0 | 0 | ... |
| | | ⋮ | ⋮ | ⋮ | ⋮ | ⋮ | ⋮ | ⋮ | ... |
| | NUMBER OF LEAVES | +1[枚] | 0 | $Q_{sub1}$ | 0 | 0 | 0 | 0 | ... |
| | | ⋮ | ⋮ | ⋮ | ⋮ | ⋮ | ⋮ | ⋮ | ... |
| | FRUIT WEIGHT | +0.5[kg] | 0 | $Q_{sub2}$ | 0 | 0 | 0 | 0 | ... |
| | | ⋮ | ⋮ | ⋮ | ⋮ | ⋮ | ⋮ | ⋮ | ... |
| ⋮ | ⋮ | ⋮ | ⋮ | ⋮ | ⋮ | ⋮ | ⋮ | ⋮ | ... |

| PORTION | CHANGE PARAMETER | | CHANGE INFORMATION | | | | | | |
|---|---|---|---|---|---|---|---|---|---|
| | | | fc1 CHANGE | fc1 Q FACTOR CHANGE | fc2 CHANGE | fc2 Q FACTOR CHANGE | fc3 CHANGE | fc3 Q FACTOR CHANGE | ... |
| | | ⋮ | ⋮ | ⋮ | ⋮ | ⋮ | ⋮ | ⋮ | ... |
| FIRST LEAF | AREA | +10.0[mm²] | 0 | Qsub3 | 0 | 0 | 0 | 0 | ... |
| | | ⋮ | ⋮ | ⋮ | ⋮ | ⋮ | ⋮ | ⋮ | ... |
| ⋮ | ⋮ | ⋮ | ⋮ | ⋮ | ⋮ | ⋮ | ⋮ | ⋮ | ... |

| PORTION | CHANGE PARAMETER | | CHANGE INFORMATION | | | | | | |
|---|---|---|---|---|---|---|---|---|---|
| | | | fc1 CHANGE | fc1 Q FACTOR CHANGE | fc2 CHANGE | fc2 Q FACTOR CHANGE | fc3 CHANGE | fc3 Q FACTOR CHANGE | ... |
| FRUIT | WEIGHT | ⋮ | ⋮ | ⋮ | ⋮ | ⋮ | ⋮ | ⋮ | ... |
| | | +0.5[kg] | 0 | 0 | 0 | 0 | +0.3[Hz] | 0 | ... |
| | | ⋮ | ⋮ | ⋮ | ⋮ | ⋮ | ⋮ | ⋮ | ... |
| ⋮ | ⋮ | ⋮ | ⋮ | ⋮ | ⋮ | ⋮ | ⋮ | ⋮ | ... |

| fc1 CHANGE | fc1 Q FACTOR CHANGE | fc2 CHANGE | fc2 Q FACTOR CHANGE | fc3 CHANGE | fc3 Q FACTOR CHANGE | ... |
|---|---|---|---|---|---|---|
| 0 | 0 | 0 | 0 | +0.33[Hz] | 0 | ... |

161

PLANT MONITORING APPARATUS, PLANT MONITORING METHOD, AND COMPUTER-READABLE RECORDING MEDIUM

INCORPORATION BY REFERENCE

This application is based upon and claims the benefit of priority from Japanese patent application No. 2019-046893, filed on Mar. 14, 2019, the disclosure of which is incorporated herein in its entirety by reference.

BACKGROUND OF THE INVENTION

1. Technical Field

The present invention relates to a plant monitoring apparatus and a plant monitoring method for monitoring plants, and also relates to a non-transitory computer-readable recording medium that stores a program for realizing the plant monitoring apparatus and the plant monitoring method.

2. Background Art

In order to monitor the growth of a plant, a method is known in which plant growth is monitored using an image capturing apparatus. For example, JP 2015-202056A discloses a system for monitoring the growth of a plant with use of captured images of the plant. According to this system for monitoring plant growth, images that correspond to a reference marker provided on a plant and a predetermined portion (measurement target) of the plant are extracted from a captured image of the plant, and the distance from the reference marker to the target portion is measured in order to monitor the growth of the plant.

Also, as related technology, JP 2015-112083A discloses an apparatus for ascertaining the health of a plant. According to this apparatus, vibration is applied to a plant with use of a vibration source, and changes in the plant are specified based on vibration measured via the plant in order to ascertain the health of the plant.

However, the plant growth monitoring system disclosed in JP 2015-202056A uses an image capturing apparatus, and therefore cannot monitor plant growth if it is not possible to capture images of the reference marker provided on the plant or the predetermined portion (measurement target) of the plant. One conceivable example is the case where a leaf, a stalk, or the like of the target plant or another plant grows and blocks the reference marker or the measurement target of the target plant in the captured image of the target plant.

Also, the plant health ascertaining apparatus disclosed in JP 2015-112083A forcibly applies vibration to the plant with use of the vibration source, and this can influence the growth of the plant. Moreover, if vibration is not forcibly applied to the plant, the health of the plant cannot be ascertained at all times.

SUMMARY

An example object of the present invention is to provide a plant monitoring apparatus, a plant monitoring method, and a program for monitoring the state of a plant with use of vibration of the plant.

In order to achieve the aforementioned object, a plant monitoring apparatus according to an example aspect of the present invention includes:

an extracting unit that extracting a feature amount in a frequency response of vibration of a target plant with use of the vibration;

a calculating unit that calculating a change that indicates growth of the plant, based on the extracted feature amount and a reference feature amount that corresponds to a reference state of the plant; and an estimating unit that estimating a state of the plant by, with use of the calculated change, referencing state information in which changes of the feature amount from the reference feature amount corresponding to growth of the plant are associated with states of the plant.

In order to achieve the aforementioned object, a plant monitoring method according to an example aspect of the present invention includes:

(a) a step of extracting a feature amount in a frequency response of vibration of a target plant with use of the vibration;

(b) a step of calculating a change that indicates growth of the plant, based on the extracted feature amount and a reference feature amount that corresponds to a reference state of the plant; and (c) a step of estimating a state of the plant by, with use of the calculated change, referencing state information in which changes of the feature amount from the reference feature amount corresponding to growth of the plant are associated with states of the plant.

In order to achieve the aforementioned object, a non-transitory computer readable recording medium according to an example aspect of the present invention includes a program recorded thereon, the program including instructions that causes a computer to carry out:

(a) a step of extracting a feature amount in a frequency response of vibration of a target plant with use of the vibration;

(b) a step of calculating a change that indicates growth of the plant, based on the extracted feature amount and a reference feature amount that corresponds to a reference state of the plant; and (c) a step of estimating a state of the plant by, with use of the calculated change, referencing state information in which changes of the feature amount from the reference feature amount corresponding to growth of the plant are associated with states of the plant.

As described above, according to the present invention, it is possible to monitor the state of a plant with use of vibration of the plant.

BRIEF DESCRIPTION OF THE DRAWINGS

FIG. 4 is a diagram showing an example of the data structure of a growth model.

FIG. 5 is a diagram showing an example of the data structure of change information.

FIG. 7 is a diagram showing an example of the data structure of a growth model according to Example Variation 1.

FIG. 9 is a diagram showing an example of the data structure of a growth model according to Example Variation 2.

FIG. 15 is a diagram showing an example of the data structure of a growth model.

FIG. 16 is a diagram showing an example of the data structure of change information.

EXEMPLARY EMBODIMENTS

First Example Embodiment

A first example embodiment of the present invention will be described below with reference to FIGS. 1 to 11.

[Apparatus Configuration]

Figure 1:
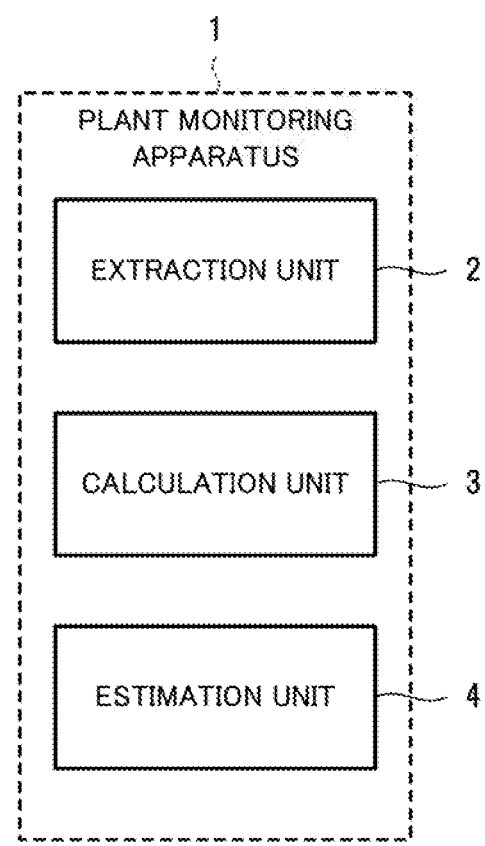
FIG. 1 is a diagram showing an example of a plant monitoring apparatus according to a first example embodiment.

First, the configuration of a plant monitoring apparatus 1 of the first example embodiment will be described using FIG. 1. FIG. 1 is a diagram showing an example of the plant monitoring apparatus of the first example embodiment.

The plant monitoring apparatus 1 shown in FIG. 1 is an apparatus that monitors the state of a plant with use of vibration of the plant. Also, as shown in FIG. 1, the plant monitoring apparatus 1 includes an extraction unit 2, a calculation unit 3, and an estimation unit 4.

The extraction unit 2 uses vibration of the target plant to extract a feature amount of a frequency response of the vibration. Based on the extracted feature amount and a reference feature amount that serves as a reference, the calculation unit 3 calculates change that indicates growth of the plant. The estimation unit 4 estimates a state of the plant by, with use of the calculated change, referencing state information (a later-described growth model) in which changes of feature amounts are associated with plant states.

In this way, in the first example embodiment, it is possible to extract a feature amount from a frequency response of vibration of the target plant, calculate the difference (change) between a reference feature amount and the extracted feature amount, and estimate plant growth (a plant state) based on the calculated change of the feature amount.

Also, in the first example embodiment, even when not forcibly applying vibration that influences plant growth, it is possible to use vibration of the plant caused by minute vibration from wind, soil shift, and the like, thus making it possible to monitor the state of the plant even when vibration is not being forcibly applied. This therefore makes it possible to continuously monitor the state of the plant.

Furthermore, because the state of the plant can be continuously monitored in the first example embodiment, the growth of the plant can be easily recorded. Furthermore, the state of the plant can be continuously monitored even when a worker is at a remote location.

[System Configuration]

Figure 2:
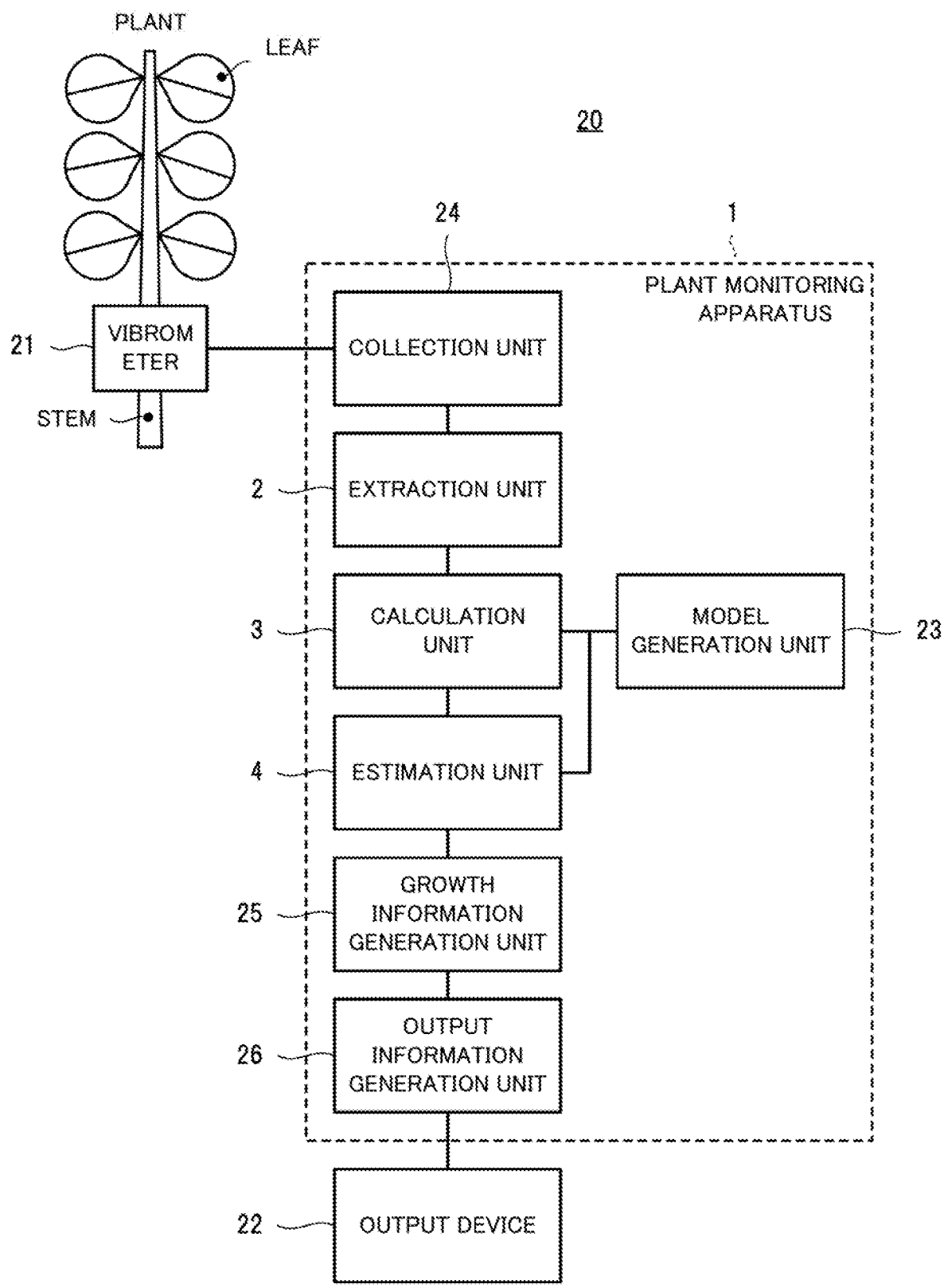
FIG. 2 is a diagram showing an example of a system that includes the plant monitoring apparatus according to the first example embodiment.

Next, the configuration of the plant monitoring apparatus 1 of the first example embodiment will be described in more detail using FIG. 2. FIG. 2 is a diagram showing an example of a system that includes the plant monitoring apparatus of the first example embodiment.

As shown in FIG. 2, a system 20 of the first example embodiment includes the plant monitoring apparatus 1, a vibrometer 21, and an output device 22. In addition to the extraction unit 2, the calculation unit 3, and the estimation unit 4, the plant monitoring apparatus 1 further includes a model generation unit 23, a collection unit 24, a growth information generation unit 25, and an output information generation unit 26.

The following describes the system 20.

The vibrometer 21 is a device that measures plant vibration generated by an external force. Specifically, the vibrometer 21 first measures plant vibration. The vibrometer 21 then outputs vibration information, which indicates the measured vibration, to the collection unit 24. External force refers to a force that applies vibration to the plant from the outside, such as wind, soil shifting, or the like. Note that the external force may apply vibration to the plant with use of an exciter or the like. It should be noted that in the case of using an exciter or the like, it is desirable that the applied vibration does not influence plant growth.

Also, the vibrometer 21 may conceivably be a mechanical, electromagnetic, piezoelectric, optical, or electromagnetic vibrometer, for example. The vibrometer 21 may also be a high-sensitivity vibration sensor such as a microphone or a miniature Michelson interferometer, for example. The vibrometer 21 and the plant monitoring apparatus 1 communicate with each other through wireless communication or wired communication, for example.

The output device 22 acquires later-described output information, which is information that has been converted into an outputtable format by the output information generation unit 26, and outputs an image, audio, or the like that has been generated based on the output information. For example, the output device 22 is a liquid crystal, organic EL (Electro Luminescence), CRT (Cathode Ray Tube), or other type of image display device. Furthermore, the image display device may include an audio output device such as a speaker. Note that the output device 22 may also be a printing device such as a printer.

The following describes the plant monitoring apparatus in more detail.

The model generation unit 23 executes a growth model simulation on a target plant in order to generate a growth model of the target plant, and stores the growth model in a storage unit (not shown). The storage unit that stores the growth model may be provided in the plant monitoring apparatus 1, or may be provided outside the plant monitoring apparatus 1.

The growth model simulation is for calculating a feature amount of the target plant in a reference state (reference feature amount) and a feature amount that changes along with growth (growth feature amount), associating change in the growth feature amount relative to the calculated reference feature amount with a plant state, and storing the result as a growth model.

Here, assuming that estimation of the growth state of the target plant is performed at a time t0, the reference state is a state of the target plant at a time that is at least before the time t0.

The following describes feature amount calculation in the growth model simulation.

(a1) First, the model generation unit 23 models the target plant in order to generate plant models. The model generation unit 23 generates a plant model for the reference state and various possible states of growth of the target plant after the reference state. Conceivable examples of various possible states of growth include a state where the stem has grown upward and a state where the stem has increased in diameter.

Also, the plant model is obtained with use of a numerical model that uses a finite element method or a mathematical model that uses a mathematical expression, for example. In the case of using a finite element method, the plant is considered to be a collection of small elastic bodies, and dynamic computer is performed for each element. If using a mathematical model, in the case of the stem of a plant growing from the ground for example, maximum approximation is performed considering the stem to be an inverted pendulum with a fixed lower portion that has restoring force, and the approximated equation of motion is used in the mathematical model.

(a2) Next, the model generation unit 23 applies vibration to some or all of the generated plant models (including the reference state) by virtually applying pre-set vibration for a pre-set time. The model generation unit 23 then measures the vibration and generates vibration information. Note that it is desirable that vibration in the plant model is measured at a position that corresponds to the position on the target plant where vibration is actually measured by the vibrometer 21. It should be noted that the position where vibration is measured in the plant model is not required to be the same as the position on the target plant where the vibrometer 21 performs measurement.

Figure 3:
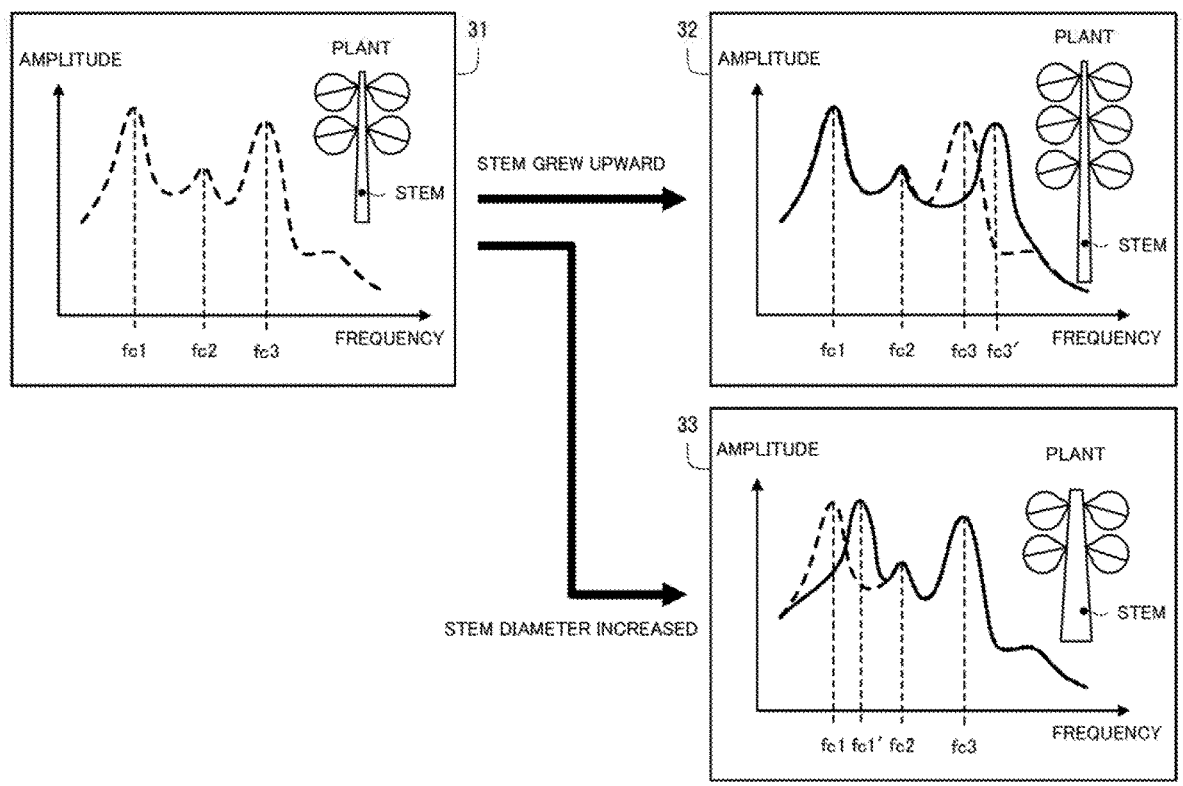
FIG. 3 is a diagram for describing frequency responses and resonance frequencies of plant models.

(a3) Next, the model generation unit 23 converts the vibration information of the generated plant models from the time domain to the frequency domain (e.g., Fourier transform) in order to generate frequency response information that indicates frequency responses as shown in FIG. 3.

FIG. 3 is a diagram for describing the frequency responses and the resonance frequencies of plant models. A graph 31 in FIG. 3 shows the frequency response of a plant model in the reference state. A graph 32 shows the frequency response of a plant model in the case where the stem of the target plant has grown upward. A graph 33 shows the frequency response of a plant model in the case where the stem of the target plant has increased in diameter.

(a4) Next, using the frequency responses of the generated plant models, the model generation unit 23 extracts, as the feature amount, either the resonance frequency or a value indicating how damped the resonance frequency is (Q factor), or both of them, from the frequency response. It should be noted that the feature amount is not limited to being the resonance frequency or the Q factor.

A graph 31 in FIG. 3 shows resonance frequencies fc1, fc2, and fc3. The graph 32 shows that the resonance frequency fc3 changes to fc3' in accordance with plant growth. The graph 33 shows that the resonance frequency fc1 changes to fc1' in accordance with plant growth.

(a5) Next, the model generation unit 23 generates plant model feature information for each plant model by associating identification information that identifies the plant model, the states of portions of the plant model, and one or more feature amounts with each other. Note that the states of portions refers to information indicating states such as the stem diameter, the stem height, and the stem inclination.

(a6) Next, the model generation unit 23 calculates the difference (change) between a feature amount that corresponds to the plant model feature information for the reference state (reference feature amount) and a feature amount that corresponds to the plant model feature information for a state of growth after the reference state (growth feature amount).

(a7) Next, the model generation unit 23 generates a growth model for each plant model as shown in FIG. 4 by associating the states of portions of the plant model, change parameters indicating change of portions of the plant model, and the changes of one or more feature amounts corresponding to the change parameters with each other, and stores the growth models in the storage unit.

FIG. 4 is a diagram showing an example of the data structure of a growth model. In a growth model 41 shown in FIG. 4, "portion", which indicates a portion of the plant model, "change parameter", which indicates states of the portion of the plant model, and "change information", which indicates change in the growth feature amounts corresponding to the reference feature amounts, are associated with each other.

The following describes the calculation of the change of feature amounts.

For example, as shown in FIG. 3, the resonance frequencies fc1, fc2, fc3 and so on are extracted in the reference plant model, and in the plant model where the stem of the reference plant model has grown upward, a resonance frequency occurs at the frequency fc3', which is different from the resonance frequency fc3, as shown in the graph 32 in FIG. 3. Also, in the plant model where the stem of the reference plant model has increased in diameter (the circumference of the stem has increased), a resonance frequency occurs at the frequency fc1', which is different from the resonance frequency fc1, as shown in the graph 33 in FIG. 3.

In such a case, if the diameter of the stem in the reference plant model has changed by a large amount such as +1.0 [mm] as in the first row of the growth model shown in FIG. 4 for example, the resonance frequency fc1' appears at a position that is shifted by +0.1 [Hz] from the resonance frequency fc1. In view of this, +1.0 [mm], which indicates the change of the diameter of the stem, which is a state of the plant ("diameter change parameter"), and +0.1 [Hz], which indicates the change of the resonance frequency in the "change information" ("fc1 change"), are stored in the storage unit in association with each other.

"Change information" such as "fc1 change", "fc1 Q factor change", "fc2 change", "fc2 Q factor change", "fc3 change", and "fc3 Q factor change", is calculated for the "change parameters" for other plant states as well (change in "diameter", "height", "inclination" and the like), and such change information is stored as shown in the growth model 41 shown in FIG. 4.

Note that the model generation unit 23 may be provided separately from the plant monitoring apparatus 1. In this case, the system is configured such that the plant monitoring apparatus 1 and the model generation unit 23 can communicate with each other.

The following describes the estimation of plant states.

The collection unit 24 collects vibration information from the vibrometer 21 in the case where the state of the target plant is to actually be estimated. Specifically, first, the collection unit 24 collects vibration information from the vibrometer 21 in a time series, and stores the vibration information in a storage unit (not shown). The storage unit may be provided in the plant monitoring apparatus 1, or may be provided outside the plant monitoring apparatus 1.

The extraction unit 2 uses the vibration information, which indicates vibration of the target plant, to generate a frequency response regarding the vibration, and extracts feature amounts from the generated frequency response.

(b1) The extraction unit 2 acquires, from the aforementioned storage unit, vibration information corresponding to a pre-set duration at a pre-set interval. Here, the set interval and the set duration can be set as desired by the user.

(b2) Next, the extraction unit 2 converts the vibration information collected over the pre-set duration from the time domain to the frequency domain (e.g., Fourier transform) to generate frequency response information that indicates the frequency response.

(b3) Next, the extraction unit 2 extracts a feature amount from the generated frequency response. The extraction unit 2 extracts a resonance frequency or a value indicating how damped the resonance frequency is (Q factor), or both, from the frequency response. It should be noted that the feature amount is not limited to being the resonance frequency or the Q factor.

The calculation unit 3 then calculates change, which indicates plant growth, based on the feature amount that was extracted by the extraction unit 2 and a reference feature amount.

(c1) First, the calculation unit 3 acquires feature information from the extraction unit 2. The calculation unit 3 also acquires plant model feature information for the reference state from the growth model.

(c2) Next, the calculation unit 3 calculates the difference (change) between a reference feature amount in the plant model feature information for the reference state and a feature amount in the feature information that was acquired from the extraction unit 2. The calculation unit 3 generates change information 51 that indicates the change of the feature amount as shown in FIG. 5 for example, and stores the change information 51 in the storage unit. FIG. 5 is a diagram showing an example of the data structure of change information.

Alternatively, instead of using the plant model, the calculation unit 3 may use feature information of the target plant that was actually measured in the reference state as the reference feature amount, and calculate the difference (change) between that reference feature amount and a feature amount in the feature information acquired from the extraction unit 2.

Then, using the calculated change information, the estimation unit 4 estimates the state of the plant by referencing the growth model, finding change information in the growth model that is similar to the calculated change information, and selecting a plant state that corresponds to the found change information.

(d1) Using the change information 51 shown in FIG. 5 that was calculated by the calculation unit 3, the estimation unit 4 references the growth model 41 shown in FIG. 4 and extracts change information that is similar to the change information 51.

(d2) Next, the estimation unit 4 selects the "change parameter" that is associated with the extracted change information 51, and estimates the plant growth indicated by the "change parameter" as the plant state. The change information 51 is similar to the change information in the first row in the growth model 41, and therefore the estimation unit 4 selects "stem diameter +10.0 [mm]" as the plant state.

Note that in the case of the change information 51 as well, the similarity calculation is performed by a method of generating a vector that has elements of the change information 51 as vector elements. A vector that has elements of the change information as vector elements is generated for each row of the growth model 41.

The distance is then calculated between the generated vector of the change information 51 and the vectors of the rows in the growth model 41, and the vector in the growth model 41 that has the shortest distance is considered to be similar to the vector of the change information 51. The distance is a Euclidian distance, for example. It should be noted that the similarity calculation method is not limited to the method described above.

The growth information generation unit 25 generates growth information by associating the plant state estimated by the estimation unit 4 with a time that indicates the time at which the vibration information was measured. The growth information generation unit 25 then stores the generated growth information in the storage unit. Note that the time at which the vibration information was measured is conceivably the date and time of the vibration information that was used in feature amount extraction, for example.

The growth information may further include a temperature, a humidity, a weather condition, a water supply amount, a fertilizer supply amount, and the like in association with the times at which such values were measured.

The output information generation unit 26 then uses the growth information to generate output information that is to be used for outputting the growth information to the output device 22. Thereafter, the output information generation unit 26 outputs the output information to the output device 22.

Example Variation 1

Figure 6:
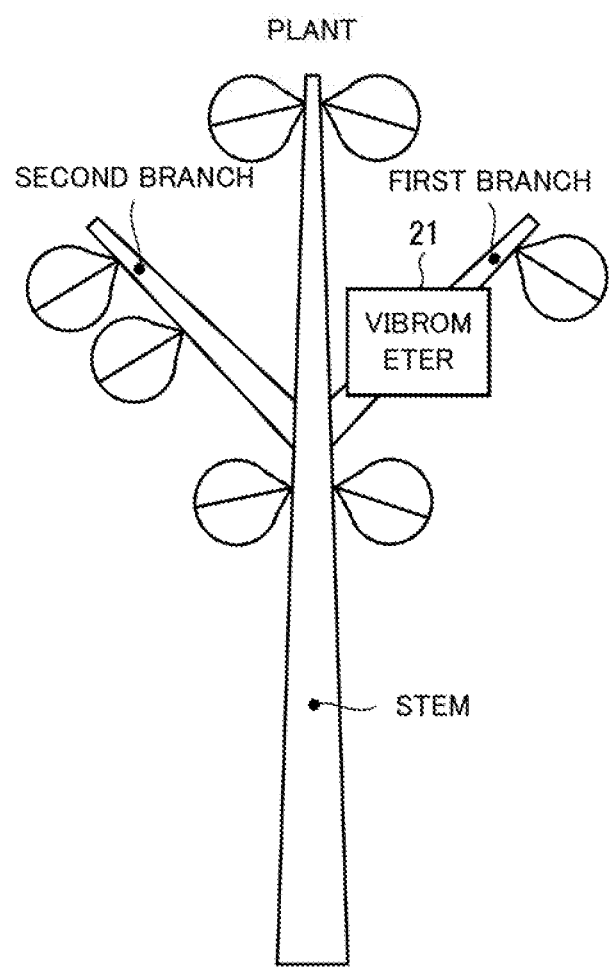
FIG. 6 is a diagram for describing the estimation of the state of a branch.

The following describes Example Variation 1. In Example Variation 1, the portion of the target plant is a branch instead of the stem. FIG. 6 is a diagram for describing the estimation of the state of a branch. Also, in the example in FIG. 6, vibration of a first branch is measured at the position of the vibrometer 21 in FIG. 6.

The following describes growth model generation in Example Variation 1.

In Example Variation 1, the model generation unit 23 executes growth model simulation on the first branch shown in FIG. 6 as the portion of the target plant, for example, in order to generate a growth model 71 that corresponds to the first branch of the target plant as shown in FIG. 7, and stores the growth model 71 in the storage unit (not shown).

FIG. 7 is a diagram showing an example of the data structure of a growth model according to Example Variation 1. In the growth model 71 shown in FIG. 7, "portion", which indicates the first branch of the plant model, "change parameter", which indicates states of the first branch of the plant model, and "change information", which indicates change in growth feature amounts corresponding to the reference feature amounts, are associated with each other.

The following describes the calculation of the change of a feature amount in Example Variation 1.

In the case of the growth model 71 shown in FIG. 7, the diameter of the first branch of the reference plant model has increased by a large amount such as +10.0 [mm], and the resonance frequency fc2' appears at a position that is shifted by +0.3 [Hz] from the resonance frequency fc2. In view of this, +10.0 [mm], which indicates the change of the "diameter" under "change parameter", which is a state of the plant, and +0.3 [Hz], which indicates the change of the resonance frequency in "fc2 change" under "change information", are stored in the storage unit in association with each other.

"Change information" such as "fc1 change", "fc1 Q factor change", "fc2 change", "fc2 Q factor change", "fc3 change", and "fc3 Q factor change", is calculated for the "change parameters" for other plant states as well (change in "diameter", "height", "number of leaves", "fruit weight", and the like), and such change information is stored as shown in the growth model 71 shown in FIG. 7.

Note that Qsub1 shown in FIG. 7 is a value that indicates that the Q factor of the reference resonance frequency fc1 has changed by Qsub1 in the case where the number of leaves on the first branch has increased by +1 [leaf]. Also, Qsub2 shown in FIG. 7 is a value that indicates that the Q factor of the reference resonance frequency fc1 has changed by Qsub2 in the case where the fruit weight of the first branch has increased by +0.5 [kg].

The following describes plant state estimation in Example Variation 1.

First, the collection unit 24 collects vibration information indicating vibration of the first branch from the vibrometer 21. Specifically, first, the collection unit 24 collects vibration information from the vibrometer 21 in a time series, and stores the vibration information in a storage unit (not shown).

Next, using the vibration information that indicates vibration of the first branch, the extraction unit 2 generates a frequency response regarding the vibration of the first branch, and extracts a feature amount of the first branch from the generated frequency response.

The calculation unit 3 then calculates change, which indicates growth of the first branch, based on the feature amount of the first branch that was extracted by the extraction unit 2 and a reference feature amount of the first branch. The calculation unit 3 then generates change information using the calculated change of the first branch, and stores the change information in the storage unit.

Alternatively, instead of using the plant model, the calculation unit 3 may use feature information of the first branch that was actually measured in the reference state as the reference feature amount, and calculate the difference (change) between that reference feature amount and a feature amount in the feature information acquired from the extraction unit 2.

Next, using the change information generated by the calculation unit 3, the estimation unit 4 references the growth model 71 and estimates a state of the first branch.

Next, the growth information generation unit 25 generates growth information in which the state of the first branch estimated by the estimation unit 4 and a time indicating the time at which the vibration information was measured are associated with each other. The growth information generation unit 25 then stores the generated growth information in the storage unit.

Note that the time at which the vibration information was measured is conceivably the date and time of the vibration information that was used in feature amount extraction, for example.

The growth information may further include a temperature, a humidity, a weather condition, a water supply amount, a fertilizer supply amount, and the like in association with the times at which such values were measured.

The output information generation unit 26 then uses the growth information to generate output information that is to be used for outputting the growth information to the output device 22. Thereafter, the output information generation unit 26 outputs the output information to the output device 22.

Example Variation 2

The following describes Example Variation 2. In Example Variation 2, the portion of the target plant is a leaf. Specifically, in Example Variation 2, vibration generated when leaves rub against each other due to an external force is measured, and leaf growth is estimated using the measured vibration.

Figure 8:
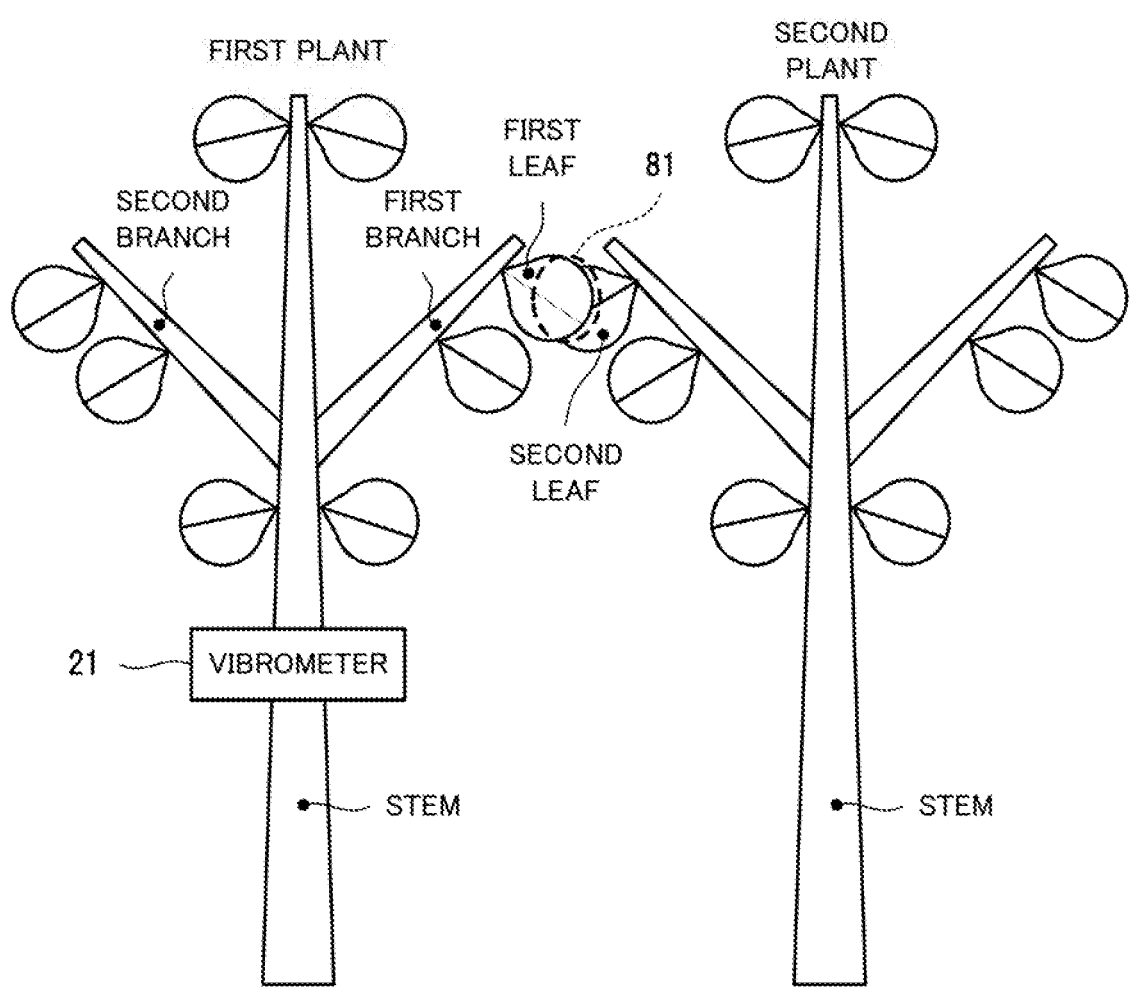
FIG. 8 is a diagram for describing the estimation of the state of a leaf.

FIG. 8 is a diagram for describing the estimation of the state of a leaf. In FIG. 8, the portion of the target plant is a leaf on the first branch as shown in FIG. 8. Also, in the example in FIG. 8, vibration generated when a first leaf and a second leaf rub against each other is measured at the position of the vibrometer 21 in FIG. 8. Note that the dashed line in FIG. 8 indicates a range 81 in which the first leaf and the second leaf rub against each other.

The following describes growth model generation in Example Variation 2.

In Example Variation 2, the model generation unit 23 executes growth model simulation on the first leaf shown in FIG. 8 as the portion of the target plant, for example, in order to generate a growth model 91 for the first leaf of the target plant as shown in FIG. 9, and stores the growth model 91 in the storage unit (not shown).

FIG. 9 is a diagram showing an example of the data structure of a growth model according to Example Variation 2. In the growth model 91 shown in FIG. 9, "portion", which indicates the first leaf of the plant model, "change parameter", which indicates states of the first leaf of the plant model, and "change information", which indicates change in growth feature amounts corresponding to the reference feature amounts, are associated with each other.

In FIG. 9, "area" under "change parameter" indicates the area of the first leaf in FIG. 8, for example. Also, the vibration generated due to the first leaf rubbing against the second leaf changes according to the areas of the first leaf and the second leaf.

The following describes growth model generation in Example Variation 2.

(a1') First, the model generation unit 23 generates plant models for the first plant and the second plant in the example shown in FIG. 8. The plant models for the first plant and the second plant are generated for a reference state and various states of change in the process of growth of the first plant and the second plant. Specifically, plant models are generated for various states of overlap of the first leaf and the second leaf in the process of growth of the first leaf and the second leaf. Note that leaf overlap is not limited to the overlapping of two leaves.

(a2') Next, the model generation unit 23 virtually applies pre-set vibration for a pre-set time to the various plant models generated using the first plant and second plant, in order to apply vibration caused by the first leaf and the second leaf rubbing against each other. The model generation unit 23 then measures the vibration and generates vibration information. Note that it is desirable that vibration in the plant model is measured at a position that corresponds to the position on the target plant where vibration is actually measured by the vibrometer 21. It should be noted that the position where vibration is measured in the plant model is not required to be the same as the position on the target plant where the vibrometer 21 performs measurement.

(a3') Next, the model generation unit 23 converts the vibration information of the plant models generated using the first plant and the second plant from the time domain to the frequency domain (e.g., Fourier transform) in order to generate frequency response information that indicates frequency responses.

(a4') Next, using the frequency responses of the generated plant models, the model generation unit 23 extracts, as the feature amount, either the resonance frequency or a value indicating how damped the resonance frequency is (Q factor), or both of them, from the frequency response. It should be noted that the feature amount is not limited to being the resonance frequency or the Q factor.

(a5') Next, the model generation unit 23 generates plant model feature information for the area of the first leaf for each plant model by associating identification information that identifies the plant model, the states of the first leaf of the plant model (change parameters), and one or more feature amounts with each other.

(a6') Next, the model generation unit 23 calculates the difference (change) between a feature amount that corresponds to the plant model feature information for the reference state (reference feature amount) and a feature amount that corresponds to the plant model feature information for a state of growth after the reference state (growth feature amount).

(a7') Next, the model generation unit 23 generates a growth model 91 shown in FIG. 9 for each plant model by associating the states of the first leaf of the plant model, change parameters indicating change of the first leaf of the plant model, and the changes of one or more feature amounts corresponding to the change parameters with each other, and stores the growth models 91 in the storage unit.

The following describes the calculation of the change of a feature amount in Example Variation 2.

In the growth model 91 shown in FIG. 9, if the area of the first leaf in the reference plant model changes by a large amount such as +10.0 [mm], the Q factor of the reference resonance frequency fc1 changes by Qsub3. In view of this, +10.0 [mm], which indicates the change of the area of the leaf, is stored as "area" under "change parameter", which is a state of the first leaf, and Qsub3, which indicates the change of the Q factor, is stored as "fc1 Q factor change" under "change information", and these values are stored in the storage unit in association with each other.

"Change information" such as "fc1 change", "fc1 Q factor change", "fc2 change", "fc2 Q factor change", "fc3 change", and "fc3 Q factor change", is calculated for the "change parameters" for other plant states as well (change in "area" and the like), and such change information is stored as shown in the growth model 91 shown in FIG. 9.

The following describes plant state estimation in Example Variation 2.

The collection unit 24 collects, from the vibrometer 21, vibration information indicating vibration generated by the first leaf and the second leaf actually rubbing against each other. Specifically, first, the collection unit 24 collects vibration information from the vibrometer 21 in a time series, and stores the vibration information in a storage unit (not shown).

Next, using the collected vibration information, the extraction unit 2 generates a frequency response regarding the vibration of the first leaf, and extracts feature amounts of the first leaf from the generated frequency response.

The calculation unit 3 then calculates change, which indicates growth of the first leaf, based on the feature amount of the first leaf that was extracted by the extraction unit 2 and a reference feature amount of the first leaf. The calculation unit 3 then generates change information using the calculated change of the first leaf, and stores the change information in the storage unit.

Alternatively, instead of using the plant model, the calculation unit 3 may use feature information of the first leaf that was actually measured in the reference state as the reference feature amount, and calculate the difference (change) between that reference feature amount and a feature amount in the feature information acquired from the extraction unit 2.

Next, using the change information generated by the calculation unit 3, the estimation unit 4 references the growth model 91 and estimates a state of the first leaf.

Next, the growth information generation unit 25 generates growth information in which the state of the first leaf estimated by the estimation unit 4 and a time indicating the time at which the vibration information was measured are associated with each other. The growth information generation unit 25 then stores the generated growth information in the storage unit. Note that the time at which the vibration information was measured is conceivably the date and time of the vibration information that was used in feature amount extraction, for example.

The growth information may further include a temperature, a humidity, a weather condition, a water supply amount, a fertilizer supply amount, and the like in association with the times at which such values were measured.

The output information generation unit 26 then uses the growth information to generate outputtable output information in order to output the growth information to the output device 22. Thereafter, the output information generation unit 26 outputs the output information to the output device 22.

[Apparatus Operation]

Figure 10:
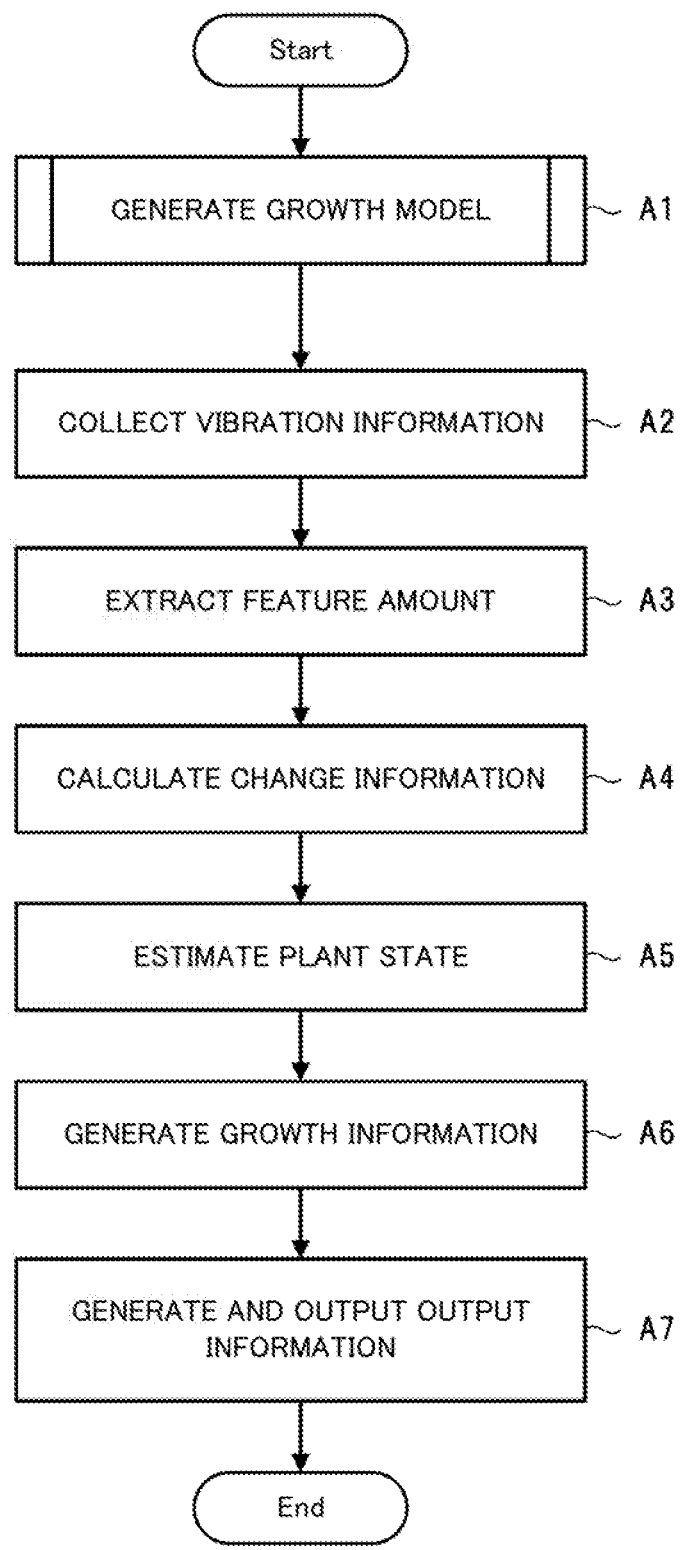
FIG. 10 is a diagram showing an example of operations of the plant monitoring apparatus according to the first example embodiment.
Figure 11:
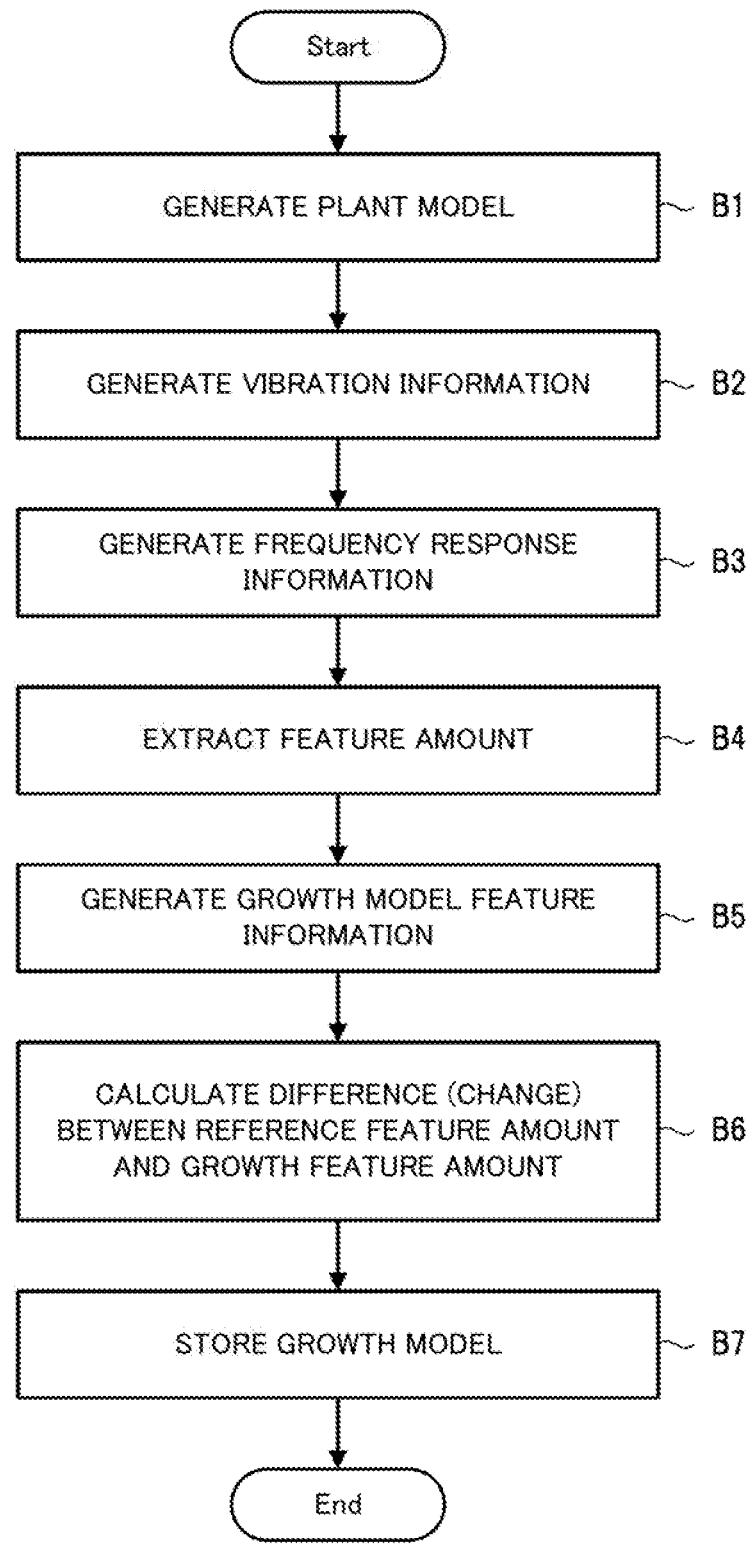
FIG. 11 is a diagram showing an example of operations of a model generation unit according to the first example embodiment.

The following describes operations of the plant monitoring apparatus according to the first example embodiment of the present invention with reference to FIGS. 10 and 11. FIG. 10 is a diagram showing an example of operations of the plant monitoring apparatus according to the first example embodiment. FIG. 11 is a diagram showing an example of operations of the model generation unit according to the first example embodiment. The following description references FIGS. 2 to 9 when appropriate. Also, in the first example embodiment, a plant monitoring method is carried out by causing the plant monitoring apparatus to operate.

Accordingly, the following description of operations of the plant monitoring apparatus will substitute for a description of a plant monitoring method according to the first example embodiment and Example Variations 1 and 2.

The following describes growth model generation with reference to FIGS. 10 and 11.

In step A1, the model generation unit 23 generates state information (growth model) indicating states of the target plant. Step A1 will be described below in more detail with reference to FIG. 11.

In step B1 (a1), first, the model generation unit 23 models the target plant in order to generate plant models.

Next, in step B2 (a2), the model generation unit 23 applies vibration to some or all of the generated plant models (including the reference state) by virtually applying pre-set vibration for a pre-set time. The model generation unit 23 then measures the vibration and generates vibration information.

Next, in step B3 (a3), the model generation unit 23 converts the vibration information of the generated plant models from the time domain to the frequency domain (e.g., Fourier transform) in order to generate frequency response information that indicates frequency responses as shown in FIG. 3.

Next, in step B4 (a4), using the frequency responses of the generated plant models, the model generation unit 23 extracts, as the feature amount, either the resonance frequency or a value indicating how damped the resonance frequency is (Q factor), or both of them, from the frequency response. It should be noted that the feature amount is not limited to being the resonance frequency or the Q factor.

Next, in step B5 (a5), the model generation unit 23 generates plant model feature information for each plant model by associating identification information that identifies the plant model, the states of portions of the plant model, and one or more feature amounts with each other.

Next, in step B6 (a6), the model generation unit 23 calculates the difference (change) between a feature amount that corresponds to the plant model feature information for the reference state (reference feature amount) and a feature amount that corresponds to the plant model feature information for a state of growth after the reference state (growth feature amount).

Next, in step B7 (a7), the model generation unit 23 generates a growth model for each plant model as shown in FIG. 4 by associating the states of portions of the plant model, change parameters indicating change of portions of the plant model, and the changes of one or more feature amounts corresponding to the change parameters with each other, and stores the growth models in the storage unit.

Note that the model generation unit 23 may be provided separately from the plant monitoring apparatus 1. In this case, the system is configured such that the plant monitoring apparatus 1 and the model generation unit 23 can communicate with each other.

The following describes the estimation of plant states with reference to FIG. 10.

In step A2, the collection unit 24 collects vibration information from the vibrometer 21 in the case where the state of the target plant is to actually be estimated. Specifically, in step A2, first, the collection unit 24 collects vibration information from the vibrometer 21 in a time series, and stores the vibration information in a storage unit (not shown). The storage unit may be provided in the plant monitoring apparatus 1, or may be provided outside the plant monitoring apparatus 1.

In step A3, the extraction unit 2 uses the vibration information, which indicates vibration of the target plant, to generate a frequency response regarding the vibration, and extracts feature amounts from the generated frequency response. In step A3, the following processing from (b1) to (b3) is performed.

(b1) In step A3, first, the extraction unit 2 acquires, from the aforementioned storage unit, vibration information corresponding to a pre-set duration at a pre-set interval. Here, the set interval and the set duration can be set as desired by the user.

(b2) Next, in step A3, the extraction unit 2 converts the vibration information collected over the pre-set duration from the time domain to the frequency domain (e.g., Fourier transform) to generate frequency response information that indicates the frequency response.

(b3) Next, in step A3, using the generated frequency responses, the extraction unit 2 extracts, as the feature amount, either the resonance frequency or a value indicating how damped the resonance frequency is (Q factor), or both of them, from the frequency response. It should be noted that the feature amount is not limited to being the resonance frequency or the Q factor.

In step A4, the calculation unit 3 then calculates change, which indicates plant growth, based on the feature amount that was extracted by the extraction unit 2 and a reference feature amount. In step A4, the following processing from (c1) to (c2) is performed.

(c1) In step A4, first, the calculation unit 3 acquires feature information from the extraction unit 2. The calculation unit 3 also acquires plant model feature information for the reference state from the growth model.

(c2) Next, in step A4, the calculation unit 3 calculates the difference (change) between a reference feature amount in the plant model feature information for the reference state and a feature amount in the feature information that was acquired from the extraction unit 2.

Alternatively, instead of using the plant model, the calculation unit 3 may use feature information of the target plant that was actually measured in the reference state as the reference feature amount, and calculate the difference (change) between that reference feature amount and a feature amount in the feature information acquired from the extraction unit 2.

In step A5, using the calculated change information, the estimation unit 4 estimates the state of the plant by referencing the growth model, finding change information in the growth model that is similar to the calculated change information, and selecting a plant state that corresponds to the found change information. In step A5, the following processing from (d1) to (d2) is performed.

(d1) In step A5, first, using the change information 51 shown in FIG. 5 that was calculated by the calculation unit 3, the estimation unit 4 references the growth model 41 shown in FIG. 4 and extracts change information that is similar to the change information 51.

(d2) Next, in step A5, the estimation unit 4 selects the "change parameter" that is associated with the extracted change information 51, and estimates the plant growth indicated by the "change parameter" as the plant state.

Next, in step A6, the growth information generation unit 25 generates growth information by associating the plant state estimated by the estimation unit 4 with a time that indicates the time at which the vibration information was measured.

Next, in step A7, the output information generation unit 26 then uses the growth information to generate outputtable output information in order to output the growth information to the output device 22. Thereafter, the output information generation unit 26 outputs the output information to the output device 22.

Example Variation 1

The following describes operations in Example Variation 1. In Example Variation 1, the portion of the target plant is a branch instead of the stem.

The following describes growth model generation in Example Variation 1.

In Example Variation 1, in step A1 (steps B1 to B7), the model generation unit 23 executes growth model simulation on the first branch shown in FIG. 6 as the portion of the target plant, for example, in order to generate a growth model 71 that corresponds to the first branch of the target plant as shown in FIG. 7, and stores the growth model 71 in the storage unit (not shown).

The following describes plant state estimation in Example Variation 1 with reference to FIG. 10.

In step A2, the collection unit 24 collects vibration information indicating vibration of the first branch from the vibrometer 21. Specifically, first, the collection unit 24 collects vibration information from the vibrometer 21 in a time series, and stores the vibration information in a storage unit (not shown).

Next, in step A3, using the vibration information that indicates vibration of the first branch, the extraction unit 2 generates a frequency response regarding the vibration of the first branch, and extracts a feature amount of the first branch from the generated frequency response.

Next, in step A4, the calculation unit 3 calculates change, which indicates growth of the first branch, based on the feature amount of the first branch that was extracted by the extraction unit 2 and a reference feature amount of the first branch. The calculation unit 3 then generates change information using the calculated change of the first branch, and stores the change information in the storage unit.

Alternatively, instead of using the plant model, the calculation unit 3 may use feature information of the first branch that was actually measured in the reference state as the reference feature amount, and calculate the difference (change) between that reference feature amount and a feature amount in the feature information acquired from the extraction unit 2.

Next, in step A5, using the change information generated by the calculation unit 3, the estimation unit 4 references the growth model 71 and estimates a state of the first branch.

Next, in step A6, the growth information generation unit 25 generates growth information by associating the first branch state estimated by the estimation unit 4 with a time that indicates the time at which the vibration information was measured. The growth information generation unit 25 then stores the generated growth information in the storage unit. Note that the time at which the vibration information was measured is conceivably the date and time of the vibration information that was used in feature amount extraction, for example.

The growth information may further include a temperature, a humidity, a weather condition, a water supply amount, a fertilizer supply amount, and the like in association with the times at which such values were measured.

Next, in step A7, the output information generation unit 26 then uses the growth information to generate outputtable output information in order to output the growth information to the output device 22. Thereafter, the output information generation unit 26 outputs the output information to the output device 22.

Example Variation 2

The following describes operations in Example Variation 2. In Example Variation 2, the portion of the target plant is a leaf. Specifically, in Example Variation 2, vibration generated when leaves rub against each other due to an external force is measured, and leaf growth is estimated using the measured vibration.

The following describes growth model generation in Example Variation 2 with reference to FIG. 11.

In Example Variation 2, the model generation unit 23 executes growth model simulation on the first leaf shown in FIG. 8 as the portion of the target plant, for example, in order to generate a growth model 91 for the first leaf of the target plant as shown in FIG. 9, and stores the growth model 91 in the storage unit (not shown).

In step B1 (a1'), first, the model generation unit 23 generates plant models for the first plant and the second plant in the example shown in FIG. 8. The plant models for the first plant and the second plant are generated for a reference state and various states of change in the process of growth of the first plant and the second plant. Note that leaf overlap is not limited to the overlapping of two leaves.

Next, in step B2 (a2'), the model generation unit 23 virtually applies pre-set vibration for a pre-set time to the various plant models generated using the first plant and second plant, in order to apply vibration caused by the first leaf and the second leaf rubbing against each other. The model generation unit 23 then measures the vibration and generates vibration information. Note that it is desirable that vibration is measured at a position that corresponds to the position on the target plant where vibration is actually measured by the vibrometer 21.

Next, in step B3 (a3'), in step A1 in Example Variation 2, the model generation unit 23 converts the vibration information of the plant models generated using the first plant and the second plant from the time domain to the frequency domain (e.g., Fourier transform) in order to generate frequency response information that indicates frequency responses.

Next, in step B4 (a4'), using the frequency responses of the generated plant models, the model generation unit 23 extracts, as the feature amount, either the resonance frequency or a value indicating how damped the resonance frequency is (Q factor), or both of them, from the frequency response. It should be noted that the feature amount is not limited to being the resonance frequency or the Q factor.

Next, in step B5 (a5'), the model generation unit 23 generates plant model feature information for the area of the first leaf for each plant model by associating identification information that identifies the plant model, the states of the first leaf of the plant model (change parameters), and one or more feature amounts with each other.

Next, in step B6 (a6'), the model generation unit 23 calculates the difference (change) between a feature amount that corresponds to the plant model feature information for the reference state (reference feature amount) and a feature amount that corresponds to the plant model feature information for a state of growth after the reference state (growth feature amount).

Next, in step B7 (a7'), the model generation unit 23 generates a growth model 91 shown in FIG. 9 for each plant model by associating the states of the first leaf of the plant model, change parameters indicating change of the first leaf of the plant model, and the changes of one or more feature amounts corresponding to the change parameters with each other, and stores the growth models 91 in the storage unit.

The following describes plant state estimation in Example Variation 2 with reference to FIG. 10.

In step A2, the collection unit 24 collects, from the vibrometer 21, vibration information indicating vibration generated by the first leaf and the second leaf actually rubbing against each other. Specifically, first, the collection unit 24 collects vibration information from the vibrometer 21 in a time series, and stores the vibration information in a storage unit (not shown).

Next, in step A3, using the collected vibration information, the extraction unit 2 generates a frequency response regarding the vibration of the first leaf, and extracts feature amounts of the first leaf from the generated frequency response.

Next, in step A4, the calculation unit 3 calculates change, which indicates growth of the first leaf, based on the feature amount of the first leaf that was extracted by the extraction unit 2 and a reference feature amount of the first leaf. The calculation unit 3 then generates change information using the calculated change of the first leaf, and stores the change information in the storage unit.

Alternatively, instead of using the plant model, the calculation unit 3 may use feature information of the first leaf that was actually measured in the reference state as the reference feature amount, and calculate the difference (change) between that reference feature amount and a feature amount in the feature information acquired from the extraction unit 2.

Next, in step A5, using the change information generated by the calculation unit 3, the estimation unit 4 references the growth model 91 and estimates a state of the first leaf.

Next, in step A6, the growth information generation unit 25 generates growth information by associating the first leaf state estimated by the estimation unit 4 with a time that indicates the time at which the vibration information was measured. The growth information generation unit 25 then stores the generated growth information in the storage unit. Note that the time at which the vibration information was measured is conceivably the date and time of the vibration information that was used in feature amount extraction, for example.

The growth information may further include a temperature, a humidity, a weather condition, a water supply amount, a fertilizer supply amount, and the like in association with the times at which such values were measured.

Next, in step A7, the output information generation unit 26 then uses the growth information to generate outputtable output information in order to output the growth information to the output device 22. Thereafter, the output information generation unit 26 outputs the output information to the output device 22.

[Effects of First Example Embodiment]

As described above, according to the first example embodiment, it is possible to extract a feature amount regarding a frequency response from the vibration of a portion of a target plant (e.g., a stem, a branch, or a leaf), calculate the difference (change) between a reference feature amount and the extracted feature amount, and estimate a plant state (plant growth state) based on the calculated change of the feature amount.

Also, in the first example embodiment, even when not forcibly applying vibration that influences plant growth, it is possible to use vibration of the plant caused by minute vibration from wind, soil shift, and the like, thus making it possible to monitor the state of the plant even when vibration is not being forcibly applied. This therefore makes it possible to continuously monitor the state of the plant.

Furthermore, because the state of the plant can be continuously monitored in the first example embodiment, the growth of the plant can be easily recorded. Furthermore, the state of the plant can be continuously monitored even when a worker is at a remote location.

[Program]

It is sufficient that a program according to the first example embodiment of the present invention is a program for causing a computer to execute steps A1 to A7 shown in FIG. 10 and steps B1 to B7 shown in FIG. 11. The plant monitoring apparatus and the plant monitoring method of the first example embodiment can be realized by installing the program in the computer and executing the program. In this case, the processor of the computer functions as, and performs processing as, the model generation unit 23, the collection unit 24, the extraction unit 2, the calculation unit 3, the estimation unit 4, the growth information generation unit 25, and the output information generation unit 26.

Also, the program of the first example embodiment may be executed by a computer system that is constructed by multiple computers. In this case, the computers may each function as, and perform processing as, any of the model generation unit 23, the collection unit 24, the extraction unit 2, the calculation unit 3, the estimation unit 4, the growth information generation unit 25, and the output information generation unit 26, for example.

Second Example Embodiment

A second example embodiment of the present invention will be described below with reference to FIGS. 12 to 18. In the second example embodiment, fruit growth can be estimated more precisely than in Example Variation 1.

[System Configuration]

Figure 12:
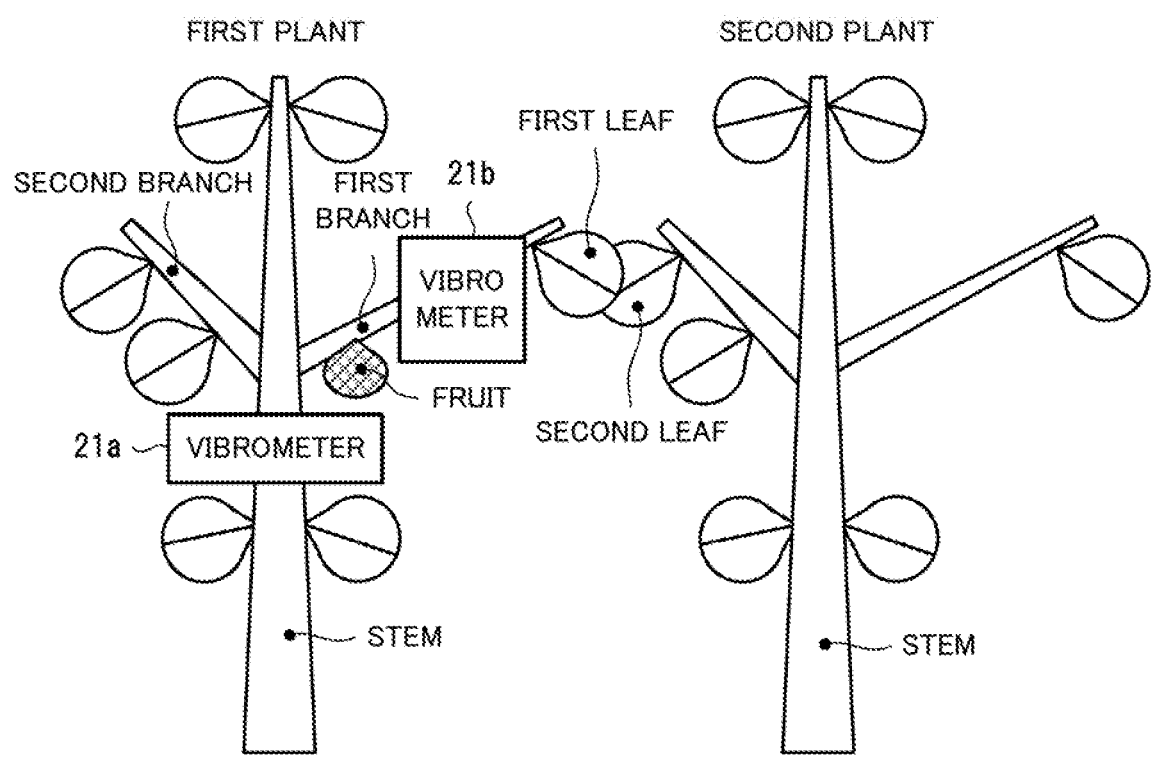
FIG. 12 is a diagram for describing the estimation of the state of a fruit.
Figure 13:
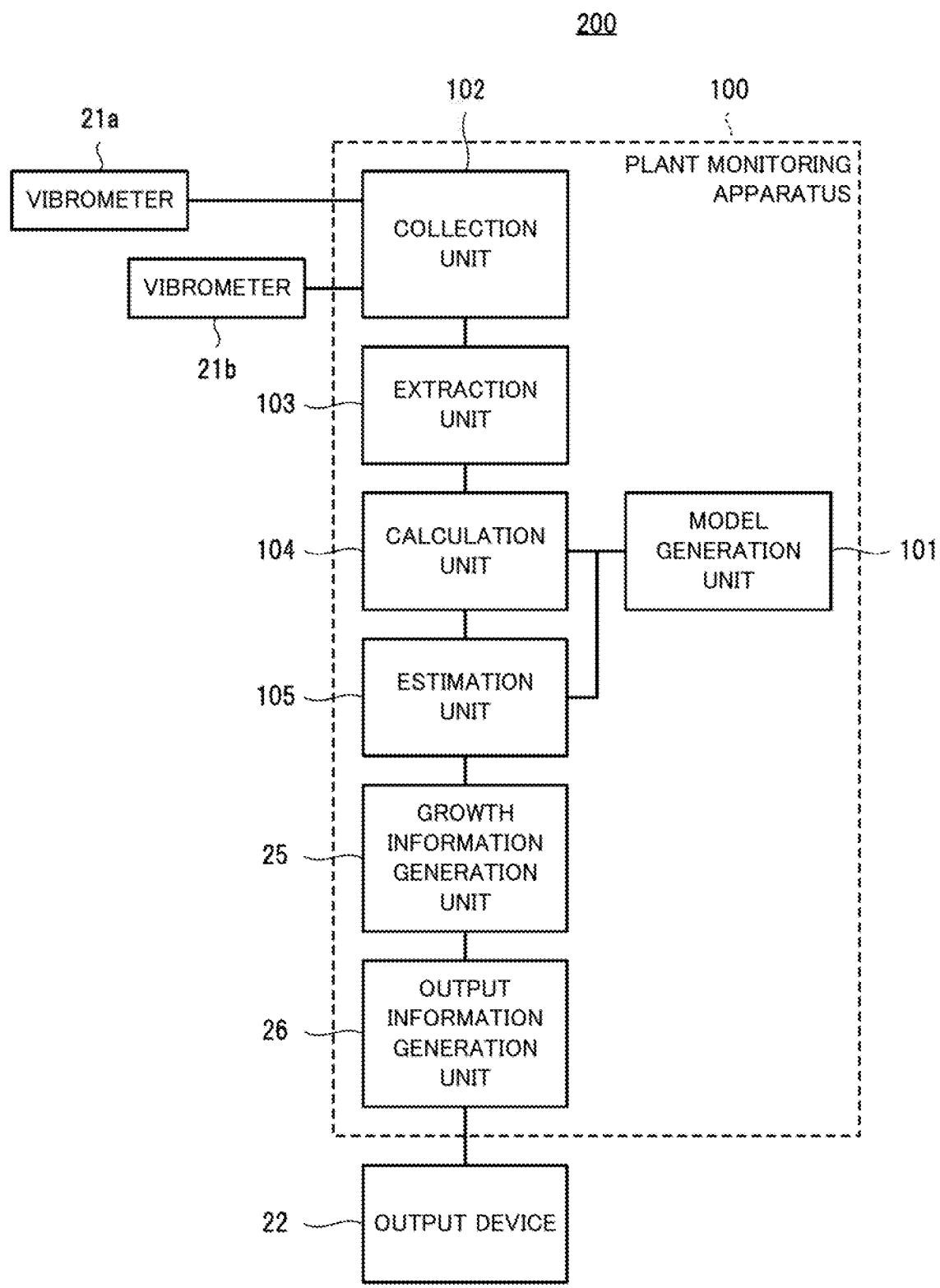
FIG. 13 is a diagram showing an example of a system that includes a plant monitoring apparatus according to a second example embodiment.

The following describes the configuration of a plant monitoring apparatus 100 of the second example embodiment and a system 200 that includes the plant monitoring apparatus 100, with reference to FIGS. 12 and 13. FIG. 12 is a diagram for describing the estimation of the state of a fruit. FIG. 13 is a diagram showing an example of the system that includes the plant monitoring apparatus according to the second example embodiment.

As shown in FIG. 12, in the second example embodiment, if a fruit is growing on a first branch, vibration of the first branch is measured using vibrometers 21a and 21b. Also, the plant monitoring apparatus 100 shown in FIG. 13 is an apparatus that monitors the state of a plant with use of vibration of the plant.

As shown in FIG. 13, the system 200 of the second example embodiment includes the vibrometers 21a and 21b, the plant monitoring apparatus 100, and an output device 22. The plant monitoring apparatus 100 includes a model generation unit 101, a collection unit 102, an extraction unit 103, a calculation unit 104, an estimation unit 105, a growth information generation unit 25, and an output information generation unit 26.

The extraction unit 103 uses vibration of the target plant measured at different locations to calculate a transfer function, and extracts a feature amount in a frequency response of the transfer function. Based on the extracted feature amount and a reference feature amount generated based on a frequency response of a reference transfer function, the calculation unit 104 calculates change that indicates growth of the plant. The estimation unit 105 estimates a plant state by, with use of the calculated change, referencing the state information in which changes of feature amounts from reference feature amounts corresponding to plant growth are associated with plant states.

The following describes the system 200.

The vibrometers 21a and 21b are devices that measure vibration of the plant caused by an external force, and transmit vibration information to the collection unit 102. Note that the vibrometers 21a and 21b are the same as the vibrometer 21 described in the first example embodiment, and therefore will not be described. The output device 22 is also the same as the output device in the first example embodiment, and therefore will not be described.

The following describes the plant monitoring apparatus in more detail.

The model generation unit 101 executes a growth model simulation on a target plant in order to generate a growth model of the target plant, and stores the growth model in a storage unit (not shown). The storage unit that stores the growth model may be provided in the plant monitoring apparatus 100, or may be provided outside the plant monitoring apparatus 100.

The growth model simulation is for calculating a feature amount of the target plant in a reference state (reference feature amount) and a feature amount that changes along with growth (growth feature amount), associating change in the growth feature amount relative to the calculated reference feature amount with a plant state, and storing the result as a growth model.

Here, assuming that estimation of the growth state of the target plant is performed at a time t0, the reference state is a state of the target plant at a time that is at least before the time t0.

The following describes feature amount calculation in the growth model simulation.

(a1") First, the model generation unit 101 models the target plant in order to generate plant models. The model generation unit 101 generates a plant model for the reference state and various possible states of growth of the target plant after the reference state. In the example shown in FIG. 12, the various possible states of growth are various possible states that a fruit on the first branch can take while growing. Also, the plant model is obtained with use of a numerical model that uses a finite element method or a mathematical model that uses a mathematical expression, for example.

(a2") Next, the model generation unit 101 applies vibration to some or all of the generated plant models (including the reference state) by virtually applying pre-set vibration for a pre-set time. The model generation unit 101 then measures the vibration and generates vibration information. Note that it is desirable that vibration in the plant model is measured at positions that correspond to the positions on the target plant where vibration is actually measured by the vibrometers 21a and 21b in the example in FIG. 12. It should be noted that the positions where vibration is measured in the plant model are not required to be the same as the positions on the target plant where the vibrometers 21a and 21b perform measurement.

(a3") Next, the model generation unit 101 calculates a transfer function $G(s)=Y(s)/X(s)=L(y(t))/L(x(t))$ for each of the generated plant models, where a signal $x(t)$ is information corresponding to the vibration information measured by the vibrometer 21a, and a signal $y(t)$ is information corresponding to the vibration information measured by the vibrometer 21b. The model generation unit 101 then generates frequency response information using the frequency responses expressed by the transfer function $G(s)$ as shown in FIG. 14.

Figure 14:
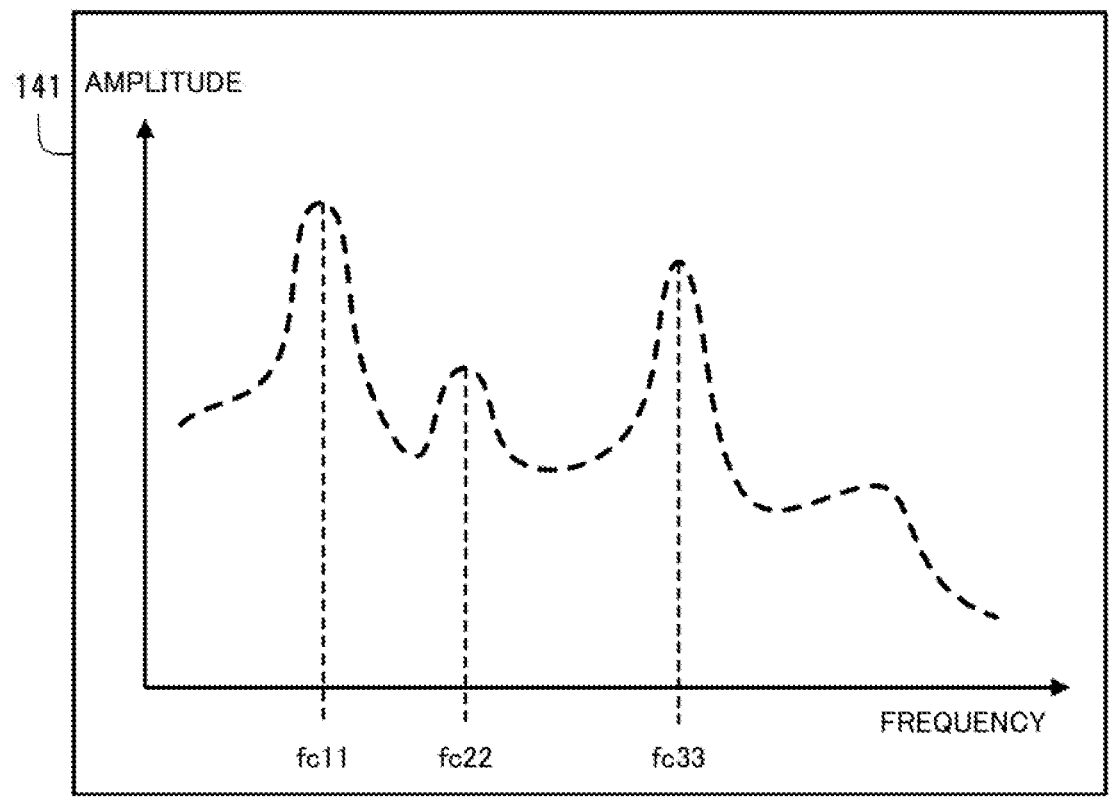
FIG. 14 is a diagram for describing frequency responses and resonance frequencies of transfer functions of plant models.
Figure 14:
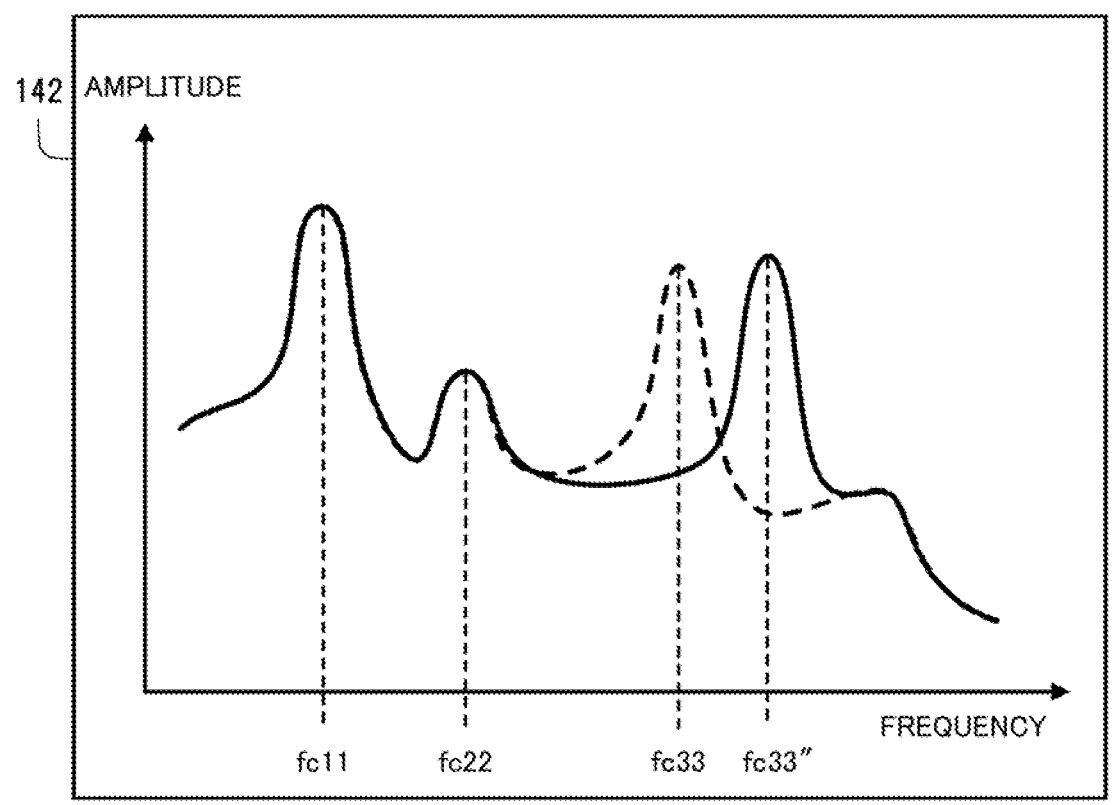

FIG. 14 is a diagram for describing the frequency responses and the resonance frequencies of transfer functions of plant models. A graph 141 in FIG. 14 shows the frequency response of a plant model in the reference state. A graph 142 shows the frequency response of a plant model in the case where a portion of the target plant has grown.

(a4") Next, using the frequency responses of the generated plant models, the model generation unit 101 extracts, as the feature amount, either the resonance frequency or a value indicating how damped the resonance frequency is (Q factor), or both of them, from the frequency response. It should be noted that the feature amount is not limited to being the resonance frequency or the Q factor.

The graph 141 in FIG. 14 shows resonance frequencies fc11, fc22, and fc33. The graph 142 shows that the resonance frequency fc3 changes to fc3" in accordance with growth of the portion.

(a5") Next, the model generation unit 101 generates plant model feature information for each plant model by associating identification information that identifies the plant model, the states of portions of the plant model, and one or more feature amounts with each other. Note that the states of portions refers to information indicating states of the fruit or the like.

(a6") Next, the model generation unit 101 calculates the difference (change) between a feature amount that corresponds to the plant model feature information for the reference state (reference feature amount) and a feature amount that corresponds to the plant model feature information for a state of growth after the reference state (growth feature amount).

(a7") Next, the model generation unit 101 generates a growth model for each plant model as shown in FIG. 15 by associating the states of portions of the plant model, change parameters indicating change of portions of the plant model, and the changes of one or more feature amounts corresponding to the change parameters with each other, and stores the growth models in the storage unit.

FIG. 15 is a diagram showing an example of the data structure of a growth model. In a growth model 151 shown in FIG. 15, "portion", which indicates a portion of the plant model, "change parameter", which indicates states of the portion of the plant model, and "change information", which indicates change in the growth feature amounts corresponding to the reference feature amounts, are associated with each other.

The following describes the calculation of the change of feature amounts.

For example, as shown in FIG. 14, the resonance frequencies fc11, fc22, fc33 and so on are extracted in the reference plant model, and in the plant model where the fruit has grown in the reference plant model, a resonance frequency occurs at the frequency fc3", which is different from the resonance frequency fc3, as shown in the graph 142 in FIG. 14.

In such a case, if the fruit weight in the reference plant model has changed by +0.5 [kg] as in the first row of the growth model shown in FIG. 15 for example, the resonance frequency fc3" appears at a position that is shifted by +0.3 [Hz] from the resonance frequency fc33. In view of this, +0.5 [kg], which indicates the change of the fruit weight, which is a state of the plant ("change parameter"), and +0.3 [Hz], which indicates the change of the resonance frequency in the "change information" ("fc3 change"), are stored in the storage unit in association with each other.

"Change information" such as "fc1 change", "fc1 Q factor change", "fc2 change", "fc2 Q factor change", "fc3 change", and "fc3 Q factor change", is calculated for the "change parameters" for other plant states as well (change in "weight" and the like), and such change information is stored as shown in the growth model 151 shown in FIG. 15.

The following describes the estimation of plant states.

The collection unit 102 collects vibration information from the vibrometers 21a and 21b in the case where the state of the target plant is to actually be estimated. Specifically, first, the collection unit 102 collects vibration information from the vibrometers 21a and 21b in a time series, and stores the vibration information in a storage unit (not shown). The storage unit may be provided in the plant monitoring apparatus 100, or may be provided outside the plant monitoring apparatus 100.

The extraction unit 103 calculates the transfer function with use of the vibration information collected by the vibrometers 21a and 21b, and extracts feature amounts from the frequency response of the calculated transfer function.

(b1") The extraction unit 103 acquires, from the aforementioned storage unit, vibration information corresponding to a pre-set duration at a pre-set interval. Here, the set interval and the set duration can be set as desired by the user.

(b2") Next, the extraction unit 103 calculates a transfer function $G(s)=Y(s)/X(s)=L(y(t))/L(x(t))$, where a signal $x(t)$ is information corresponding to the vibration information measured by the vibrometer 21a, and a signal $y(t)$ is information corresponding to the vibration information measured by the vibrometer 21b. The extraction unit 103 then generates frequency response information using the frequency responses expressed by the transfer function $G(s)$.

(b3") Next, the extraction unit 103 extracts a feature amount from the generated frequency response. The extraction unit 103 extracts a resonance frequency or a value indicating how damped the resonance frequency is (Q factor), or both, from the frequency response. It should be noted that the feature amount is not limited to being the resonance frequency or the Q factor.

The calculation unit 104 then calculates change, which indicates plant growth, based on the feature amount that was extracted by the extraction unit 103 and a reference feature amount.

(c1") First, the calculation unit 104 acquires feature information from the extraction unit 103. The calculation unit 104 also acquires plant model feature information for the reference state from the growth model.

(c2") Next, the calculation unit 104 calculates the difference (change) between a reference feature amount in the plant model feature information for the reference state and a feature amount in the feature information that was acquired from the extraction unit 103. The calculation unit 104 generates change information 161 that indicates the change of the feature amount as shown in FIG. 16 for example, and stores the change information 161 in the storage unit. FIG. 16 is a diagram showing an example of the data structure of change information.

Alternatively, instead of using the plant model, the calculation unit 104 may use feature information of the target plant that was actually measured in the reference state as the reference feature amount, and calculate the difference (change) between that reference feature amount and a feature amount in the feature information acquired from the extraction unit 103.

Then, using the calculated change information, the estimation unit 105 estimates the state of the plant by referencing the growth model, finding change information in the growth model that is similar to the calculated change information, and selecting a plant state that corresponds to the found change information.

(d1") Using the change information 161 shown in FIG. 16 that was calculated by the calculation unit 104, the estimation unit 105 references the growth model 151 shown in FIG. 15 and extracts change information that is similar to the change information 161.

(d2") Next, the estimation unit 105 selects the "change parameter" that is associated with the extracted change information 161, and estimates the growth of the portion of the plant indicated by the "change parameter" as the plant state. The change information 161 is similar to the change information in the first row in the growth model 151, and therefore the estimation unit 105 selects "fruit weight +0.5 [kg]" as the plant state.

The growth information generation unit 25 generates growth information by associating the plant portion state estimated by the estimation unit 105 with a time that indicates the time at which the vibration information was measured. The growth information generation unit 25 then stores the generated growth information in the storage unit. Note that the time at which the vibration information was measured is conceivably the date and time of the vibration information that was used in feature amount extraction, for example.

The growth information may further include a temperature, a humidity, a weather condition, a water supply amount, a fertilizer supply amount, and the like in association with the times at which such values were measured.

The output information generation unit 26 then uses the growth information to generate output information that is to be used for outputting the growth information to the output device 22. Thereafter, the output information generation unit 26 outputs the output information to the output device 22.

[Apparatus Operation]

Figure 17:
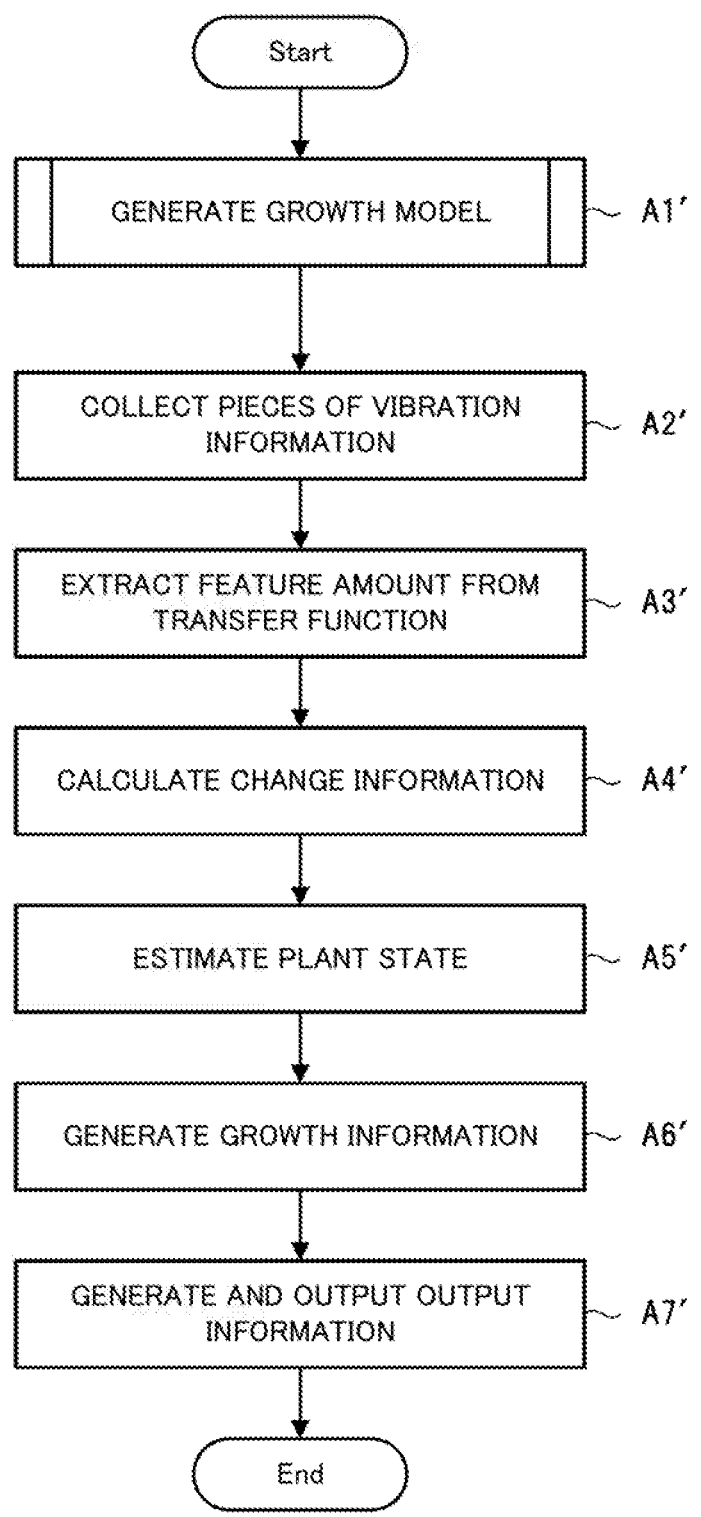
FIG. 17 is a diagram showing an example of operations of the plant monitoring apparatus according to the second example embodiment.
Figure 18:
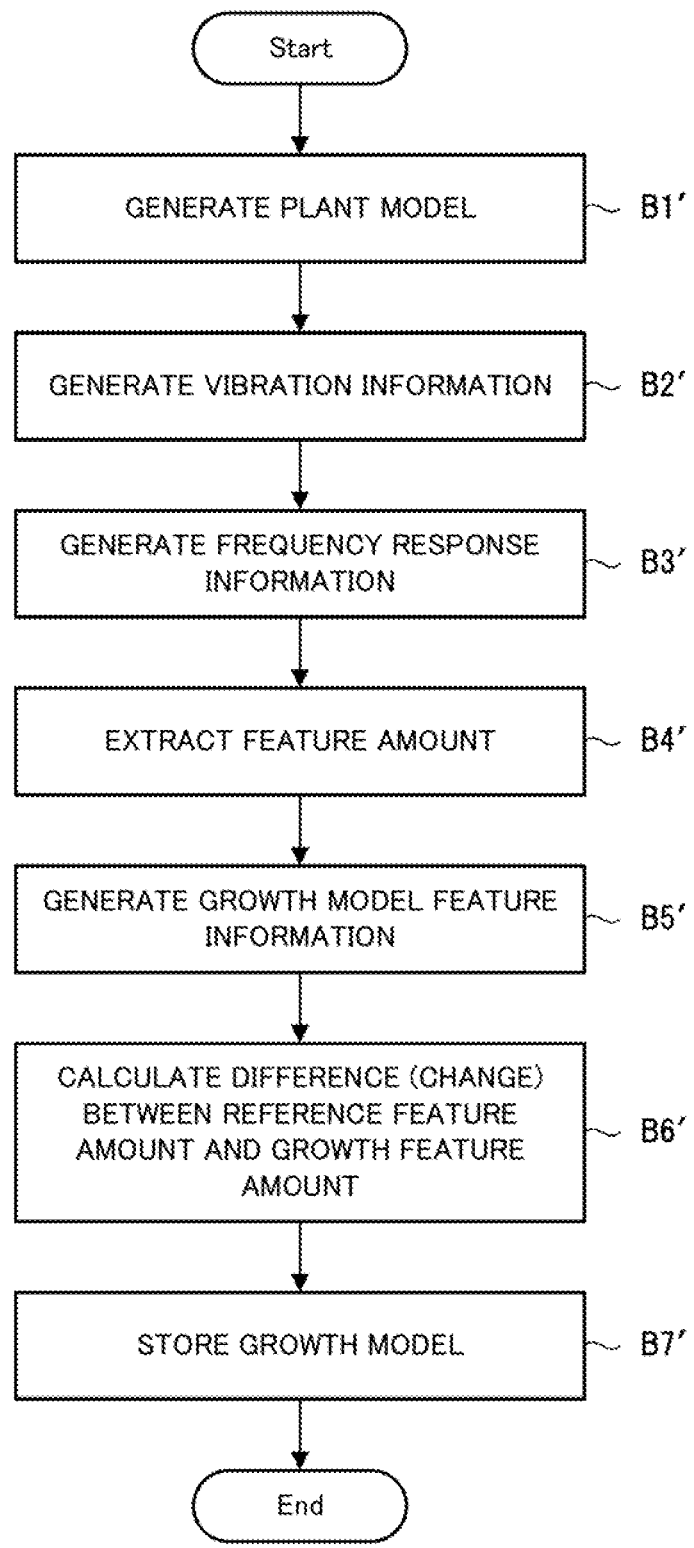
FIG. 18 is a diagram showing an example of operations of a model generation unit according to the second example embodiment.

The following describes operations of the plant monitoring apparatus according to the second example embodiment of the present invention with reference to FIGS. 17 and 18. FIG. 17 is a diagram showing an example of operations of the plant monitoring apparatus according to the second example embodiment. FIG. 18 is a diagram showing an example of operations of the model generation unit according to the second example embodiment. The following description references FIGS. 12 to 16 when appropriate. Also, in the second example embodiment, a plant monitoring method is carried out by causing the plant monitoring apparatus to operate. Accordingly, the following description of operations of the plant monitoring apparatus will substitute for a description of a plant monitoring method according to the second example embodiment.

The following describes growth model generation with reference to FIGS. 17 and 18.

In step A1' in FIG. 17, the model generation unit 101 generates state information (growth model) indicating states of the target plant. Step A1' will be described below in more detail with reference to FIG. 18.

In step B1' (a1"), first, the model generation unit 101 models the target plant in order to generate plant models.

Next, in step B2' (a2"), the model generation unit 101 applies vibration to some or all of the generated plant models (including the reference state) by virtually applying pre-set vibration for a pre-set time. The model generation unit 101 then measures the vibration and generates vibration information. Note that it is desirable that vibration in the plant model is measured at positions that correspond to the positions on the target plant where vibration is actually measured by the vibrometers 21a and 21b in the example in FIG. 12. It should be noted that the positions where vibration is measured in the plant model are not required to be the same as the positions on the target plant where the vibrometers 21a and 21b perform measurement.

Next, in step B3' (a3") the model generation unit 101 calculates a transfer function $G(s)=Y(s)/X(s)=L(y(t))/L(x(t))$ for each of the generated plant models, where a signal $x(t)$ is information corresponding to the vibration information measured by the vibrometer 21a, and a signal $y(t)$ is information corresponding to the vibration information measured by the vibrometer 21b. The model generation unit 101 then generates frequency response information using the frequency responses expressed by the transfer function G(s) as shown in FIG. 14.

Next, in step B4' (a4"), using the frequency responses of the generated plant models, the model generation unit 101 extracts, as the feature amount, either the resonance frequency or a value indicating how damped the resonance frequency is (Q factor), or both of them, from the frequency response. It should be noted that the feature amount is not limited to being the resonance frequency or the Q factor.

Next, in step B5' (a5"), the model generation unit 101 generates plant model feature information for each plant model by associating identification information that identifies the plant model, the states of portions of the plant model, and one or more feature amounts with each other. Note that the states of portions refers to information indicating states of the fruit or the like.

Next, in step B6' (a6"), the model generation unit 101 calculates the difference (change) between a feature amount that corresponds to the plant model feature information for the reference state (reference feature amount) and a feature amount that corresponds to the plant model feature information for a state of growth after the reference state (growth feature amount).

Next, in step B7' (a7"), the model generation unit 101 generates a growth model for each plant model as shown in FIG. 15 by associating the states of portions of the plant model, change parameters indicating change of portions of the plant model, and the changes of one or more feature amounts corresponding to the change parameters with each other, and stores the growth models in the storage unit.

The following describes the estimation of plant states with reference to FIG. 17.

In step A2', the collection unit 102 collects vibration information from the vibrometers 21a and 21b in the case where the state of the target plant is to actually be estimated. Specifically, in step A2', first, the collection unit 102 collects vibration information from the vibrometers 21a and 21b in a time series, and stores the vibration information in a storage unit (not shown). The storage unit may be provided in the plant monitoring apparatus 100, or may be provided outside the plant monitoring apparatus 100.

In step A3', the extraction unit 103 calculates the transfer function with use of the vibration information collected by the vibrometers 21a and 21b, and extracts feature amounts from the frequency response of the calculated transfer function. In step A3, the following processing from (b1") to (b3") is performed.

(b1") In step A3', first, the extraction unit 103 acquires, from the aforementioned storage unit, vibration information corresponding to a pre-set duration at a pre-set interval. Here, the set interval and the set duration can be set as desired by the user.

(b2") Next, in step A3', the extraction unit 103 calculates a transfer function G"(s)=Y(s)/X(s)=L(y(t))/L(x(t)), where a signal x(t) is information corresponding to the vibration information measured by the vibrometer 21a, and a signal y(t) is information corresponding to the vibration information measured by the vibrometer 21b. The extraction unit 103 then generates frequency response information using the frequency responses expressed by the transfer function G(s).

(b3") Next, in step A3', the extraction unit 103 extracts a feature amount from the generated frequency response. The extraction unit 103 extracts a resonance frequency or a value indicating how damped the resonance frequency is (Q factor), or both, from the frequency response. It should be noted that the feature amount is not limited to being the resonance frequency or the Q factor.

In step A4', the calculation unit 104 then calculates change, which indicates plant growth, based on the feature amount that was extracted by the extraction unit 103 and a reference feature amount. In step A4', the following processing from (c1") to (c2") is performed.

(c1") First, in step A4', the calculation unit 104 acquires feature information from the extraction unit 103. The calculation unit 104 also acquires plant model feature information for the reference state from the growth model.

(c2") Next, in step A4', the calculation unit 104 calculates the difference (change) between a reference feature amount in the plant model feature information for the reference state and a feature amount in the feature information that was acquired from the extraction unit 103.

Alternatively, instead of using the plant model, the calculation unit 104 may use feature information of the target plant that was actually measured in the reference state as the reference feature amount, and calculate the difference (change) between that reference feature amount and a feature amount in the feature information acquired from the extraction unit 103.

In step A5', using the calculated change information, the estimation unit 105 estimates the state of the plant by referencing the growth model, finding change information in the growth model that is similar to the calculated change information, and selecting a plant state that corresponds to the found change information.

In step A5', the following processing from (d1") to (d2") is performed.

(d1") In step A5', using the change information 161 shown in FIG. 16 that was calculated by the calculation unit 104, the estimation unit 105 references the growth model 151 shown in FIG. 15 and extracts change information that is similar to the change information 161.

(d2") Next, in step A5', the estimation unit 105 selects the "change parameter" that is associated with the extracted change information 161, and estimates the growth of the portion of the plant indicated by the "change parameter" as the plant state.

Next, in step A6', the growth information generation unit 25 generates growth information by associating the plant state estimated by the estimation unit 103 with a time that indicates the time at which the vibration information was measured.

Next, in step A7', the output information generation unit 26 then uses the growth information to generate outputtable output information in order to output the growth information to the output device 22. Thereafter, the output information generation unit 26 outputs the output information to the output device 22.

[Effects of Second Example Embodiment]

As described above, according to the second example embodiment, it is possible to extract a feature amount regarding a transfer function from the vibration of a portion of a target plant (e.g., a fruit), calculate the difference (change) between a reference feature amount and the extracted feature amount, and estimate a plant portion state (plant portion growth state) based on the calculated change of the feature amount.

Also, in the second example embodiment, even when not forcibly applying vibration that influences plant growth, it is possible to use vibration of the portion of the plant caused by minute vibration from wind, soil shift, and the like, thus making it possible to monitor the state of the plant even when vibration is not being forcibly applied. This therefore makes it possible to continuously monitor the state of the plant.

Furthermore, because the state of the portion of the plant can be continuously monitored in the second example embodiment, the growth of the portion of the plant can be easily recorded. Furthermore, the state of the plant can be continuously monitored even when a worker is at a remote location.

[Program]

It is sufficient that a program according to the second example embodiment of the present invention is a program for causing a computer to execute steps A1' to A7' shown in FIG. 17 and steps B1' to B7' shown in FIG. 18. The plant monitoring apparatus and the plant monitoring method of the second example embodiment can be realized by installing the program in the computer and executing the program. In this case, the processor of the computer functions as, and performs processing as, the model generation unit 101, the collection unit 102, the extraction unit 103, the calculation unit 104, the estimation unit 105, the growth information generation unit 25, and the output information generation unit 26.

Also, the program of the second example embodiment may be executed by a computer system that is constructed by multiple computers. In this case, the computers may each function as, and perform processing as, any of the model generation unit 101, the collection unit 102, the extraction unit 103, the calculation unit 104, the estimation unit 105, the growth information generation unit 25, and the output information generation unit 26, for example.

[Physical Configuration]

Figure 19:
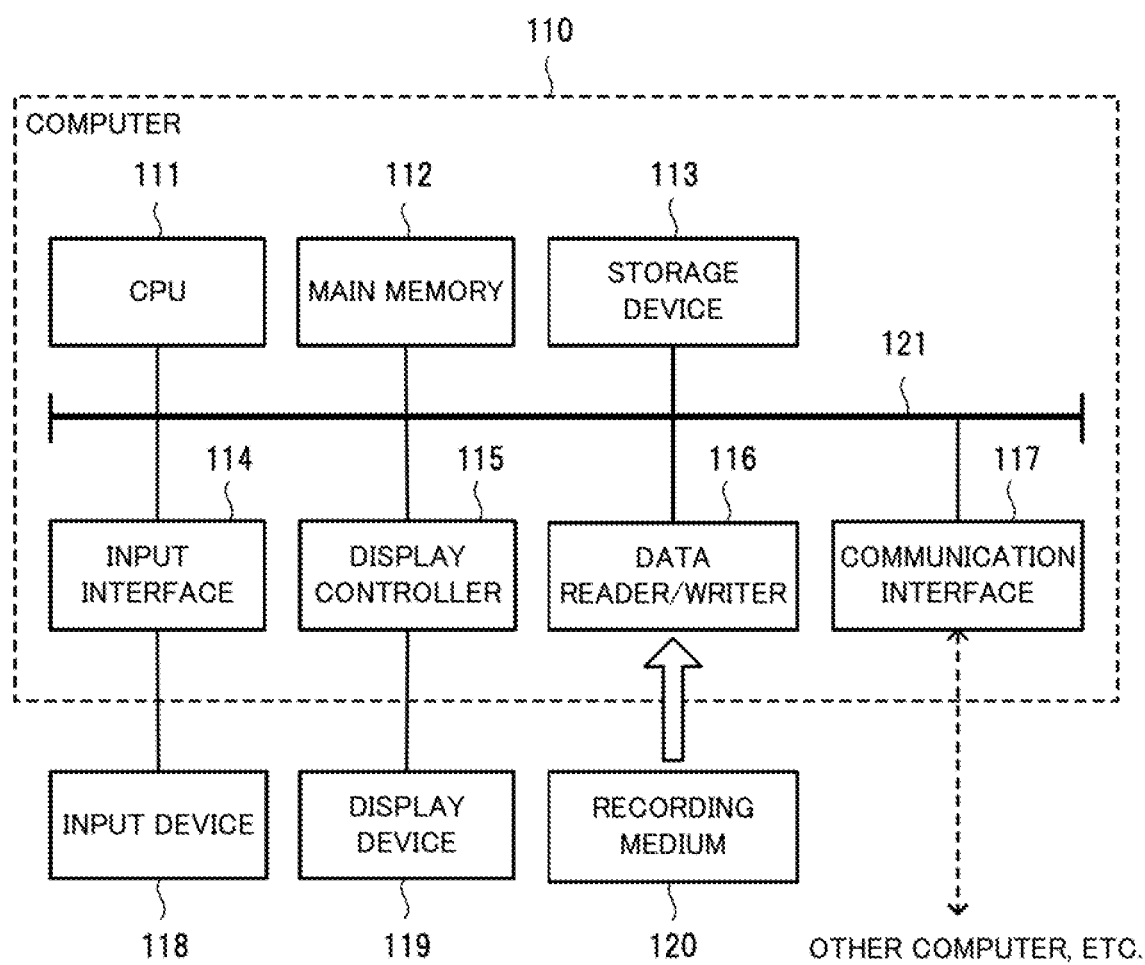
FIG. 19 is a diagram showing an example of a computer that realizes the plant monitoring apparatus according to the first or second example embodiment.

A computer that realizes the plant monitoring apparatus by executing the program of the first and second example embodiments will be described below with reference to FIG. 19. FIG. 19 is a block diagram showing an example of the computer that realizes the plant monitoring apparatus according to the first and second example embodiments of the present invention.

As shown in FIG. 19, a computer 110 includes a CPU 111, a main memory 112, a storage device 113, an input interface 114, a display controller 115, a data reader/writer 116, and a communication interface 117. These members are connected via a bus 121 to enable the exchange of data therebetween. Note that the computer 110 may include a GPU (Graphics Processing Unit) or an FPGA (Field-Programmable Gate Array) in addition to the CPU 111 or instead of the CPU 111.

The CPU 111 carries out various types of arithmetic calculation by loading the program (code) of the example embodiments, which is stored in the storage device 113, to the main memory 112 and executing portions of the program in a predetermined sequence. The main memory 112 is typically a volatile storage device such as a DRAM (Dynamic Random Access Memory). Also, the program of the example embodiments is provided in a state of being stored on a computer readable recording medium 120. Note that the program of the example embodiments may be distributed over the Internet, which can be accessed via the communication interface 117.

Besides a hard disk drive, other examples of the storage device 113 include a semiconductor storage device such as a flash memory. The input interface 114 mediates the transfer of data between the CPU 111 and input devices 118 such as a keyboard and a mouse. The display controller 115 is connected to a display device 119 and controls display performed by the display device 119.

The data reader/writer 116 mediates the transfer of data between the CPU 111 and the recording medium 120, reads out the program from the recording medium 120, and writes processing results obtained by the computer 110 to the recording medium 120. The communication interface 117 mediates the transfer of data between the CPU 111 and other computers.

Examples of the recording medium 120 include a general-purpose semiconductor storage device such as a CF (Compact Flash (registered trademark)) or an SD (Secure Digital) card, a magnetic recording medium such as a flexible disk, and an optical recording medium such as a CD-ROM (Compact Disk Read Only Memory).

The following discloses supplementary notes regarding the example embodiments described above. The example embodiments described above can be partially or entirely realized by Supplementary Notes 1 to 12 listed below, but the present invention is not limited to the following descriptions.

(Supplementary Note 1)

A plant monitoring apparatus including:

an extracting unit for extracting a feature amount in a frequency response of vibration of a target plant with use of the vibration;

a calculating unit for calculating a change that indicates growth of the plant, based on the extracted feature amount and a reference feature amount that corresponds to a reference state of the plant; and an estimating unit for estimating a state of the plant by, with use of the calculated change, referencing state information in which changes of the feature amount from the reference feature amount corresponding to growth of the plant are associated with states of the plant.

(Supplementary Note 2)

The plant monitoring apparatus according to Supplementary note 1, wherein the extracting unit extracts a feature amount in a frequency response that corresponds to growth of a portion of the plant with use of vibration of the portion of the plant, the calculating unit calculates a change that indicates growth of the portion based on the extracted feature amount of the portion and a reference feature amount of the portion, and the estimating unit estimates a state of the portion by, with use of the calculated change that indicates growth of the portion, referencing state information in which changes of the feature amount of the portion from the reference feature amount of the portion corresponding to growth of the portion are associated with states of the portion.

(Supplementary Note 3)

The plant monitoring apparatus according to Supplementary note 2, wherein the portion is a stem, a branch, or a leaf of the plant.

(Supplementary Note 4)

A plant monitoring apparatus including:

an extracting unit for calculating a transfer function with use of vibration of a target plant measured at a plurality of different locations, and extracting a feature amount in a frequency response of the transfer function;

a calculating unit for calculating a change that indicates growth of the plant, based on the extracted feature amount and a reference feature amount generated based on a frequency response of a reference transfer function; and an estimating unit for estimating a state of the plant by, with use of the calculated change, referencing state information in which changes of the feature amount from the reference feature amount corresponding to growth of the plant are associated with states of the plant.

(Supplementary Note 5)

A plant monitoring method including:

(a) extracting a feature amount in a frequency response of vibration of a target plant with use of the vibration;

(b) calculating a change that indicates growth of the plant, based on the extracted feature amount and a reference feature amount that corresponds to a reference state of the plant; and (c) estimating a state of the plant by, with use of the calculated change, referencing state information in which changes of the feature amount from the reference feature amount corresponding to growth of the plant are associated with states of the plant.

(Supplementary Note 6)

The plant monitoring method according to Supplementary note 5, wherein in the (a), a feature amount in a frequency response that corresponds to growth of a portion of the plant is extracted with use of vibration of the portion of the plant, in the (b), a change that indicates growth of the portion is calculated based on the extracted feature amount of the portion and a reference feature amount of the portion, and in the (c), a state of the portion is estimated by, with use of the calculated change that indicates growth of the portion, referencing state information in which changes of the feature amount of the portion from the reference feature amount of the portion corresponding to growth of the portion are associated with states of the portion.

(Supplementary Note 7)

The plant monitoring method according to Supplementary note 6, wherein the portion is a stem, a branch, or a leaf of the plant.

(Supplementary Note 8)

A plant monitoring method including:

(a) calculating a transfer function with use of vibration of a target plant measured at a plurality of different locations, and extracting a feature amount in a frequency response of the transfer function;

(b) calculating a change that indicates growth of the plant, based on the extracted feature amount and a reference feature amount generated based on a frequency response of a reference transfer function; and (c) estimating a state of the plant by, with use of the calculated change, referencing state information in which changes of the feature amount from the reference feature amount corresponding to growth of the plant are associated with states of the plant.

(Supplementary Note 9)

A non-transitory computer readable recording medium that includes a program recorded thereon, the program including instructions that causes a computer to carry out:

(a) a step of extracting a feature amount in a frequency response of vibration of a target plant with use of the vibration;

(b) a step of calculating a change that indicates growth of the plant, based on the extracted feature amount and a reference feature amount that corresponds to a reference state of the plant; and (c) a step of estimating a state of the plant by, with use of the calculated change, referencing state information in which changes of the feature amount from the reference feature amount corresponding to growth of the plant are associated with states of the plant.

(Supplementary Note 10)

The non-transitory computer readable recording medium according to Supplementary note 9, wherein in the (a) step, a feature amount in a frequency response that corresponds to growth of a portion of the plant is extracted with use of vibration of the portion of the plant, in the (b) step, a change that indicates growth of the portion is calculated based on the extracted feature amount of the portion and a reference feature amount of the portion, and in the (c) step, a state of the portion is estimated by, with use of the calculated change that indicates growth of the portion, referencing state information in which changes of the feature amount of the portion from the reference feature amount of the portion corresponding to growth of the portion are associated with states of the portion.

(Supplementary Note 11)

The non-transitory computer readable recording medium according to Supplementary note 10, wherein the portion is a stem, a branch, or a leaf of the plant.

(Supplementary Note 12)

A non-transitory computer readable recording medium that includes a program recorded thereon, the program including instructions that causes a computer to carry out:

(a) a step of calculating a transfer function with use of vibration of a target plant measured at a plurality of different locations, and extracting a feature amount in a frequency response of the transfer function;

(b) a step of calculating a change that indicates growth of the plant, based on the extracted feature amount and a reference feature amount generated based on a frequency response of a reference transfer function; and (c) a step of estimating a state of the plant by, with use of the calculated change, referencing state information in which changes of the feature amount from the reference feature amount corresponding to growth of the plant are associated with states of the plant.

As described above, the present invention enables monitoring the state of a plant with use of vibration of the plant. The present invention is applicable to fields that require the monitoring of the state of a plant (plant growth).

While the invention has been particularly shown and described with reference to exemplary embodiments thereof, the invention is not limited to these embodiments. It will be understood by those of ordinary skill in the art that various changes in form and details may be made therein without departing from the spirit and scope of the present invention as defined by the claims.

What is claimed is:

1. A plant monitoring method executed by a computer, comprising:

executing a growth model simulation on a target plant to generate a growth model with respect to a plurality of portions of the target plant by:
  i) modeling a target plant to generate a plurality of plant models with respect to respective one or more states of the plurality of portions,
  ii) virtually applying vibration to the plant models to generate vibration information of each of the plant models in a time domain,
  iii) converting the vibration information into a frequency domain to generate a frequency response per plant model,
  iv) calculating a first feature modeled amount per plant model based on the generated frequency response,
  v) calculating a first difference, per plant model, between the first feature modeled amount of the plant model and a reference feature amount, and generating a first growth model for each plant model by associating information for identifying a growth state of the plurality of portions corresponding to said plant model, a plurality of growth amounts of each identified growth state of the plurality of portions, and the calculated first differences corresponding to the plurality of growth amounts, the reference feature amount being a feature amount in a growth reference state of the target plant;

directly measured from the plurality of portion of the target plant, acquiring vibration information in a time domain, which has been generated by a plurality of vibrometers configured to apply vibration to each of the plurality of portions of the target plant and configured to receive the vibration information from each of the plurality of portions of the target plantby, each of the vibrometers further configured to transmit the received vibration information to a collection unit configured to convert the vibration information from each of the vibrometers into a frequency domain to generate a frequency response, and extracting a second feature measured amount from the generated frequency response; calculating a second difference between the extracted second feature measured amount and the reference feature amount; estimating a measured growth amount of the plurality of portions of the target plant by referencing the growth model, selecting a first difference, among the plurality of first modeled differences of each of the growth states, that is similar to the extracted second measured difference, acquiring a growth amount associated with the selected first modeled difference, wherein each of the reference feature amount, the first feature modeled amount, and the second feature measured amount have at least a resonance frequency and a Q value representing a sharpness of the resonance frequency; and iteratively monitoring and outputting growth information for each of the plurality of portions of the target plant and correlating at least two or more portions of growth information from two or more vibrometers to obtain a secondary growth state of the target plant.

2. The plant monitoring method according to claim 1, wherein the each of the plurality of portions is a stem, a branch, or a leaf of the plant.

3. A plant monitoring apparatus comprising: at least one memory configured to store one or more instructions; and at least one processor configured to execute the one or more instructions to:
  a growth model simulation on a target plant to generate a growth model with respect to a plurality of portions of the target plant by:
    i) modeling a target plant to generate a plurality of plant models with respect to respective one or more states of the plurality of portions,
    ii) virtually applying vibration to the plant models to generate vibration information of each of the plant models in a time domain,
    iii) converting the vibration information into a frequency domain to generate a frequency response per plant model, calculating a first feature modeled amount per plant model based on the generated frequency response,
    iv) calculating a first difference, per plant model, between the first feature modeled amount of the plant model and a reference feature amount, and
    v) generating a first growth model for each plant model by associating information for identifying a growth state of the plurality of portions corresponding to said plant model, a plurality of growth amounts of each identified growth state of the plurality of portions, and the calculated first differences corresponding to the plurality of growth amounts, the reference feature amount being a feature amount in a growth reference state of the target plant;

directly measured from the plurality of portion of the target plant, acquire vibration information in a time domain, which has been generated by a plurality of vibrometers configured to apply vibration to each of the plurality of portions of the target plant and configured to receive the vibration information from each of the plurality of portions of the target plant by, each of the vibrometers further configured to transmit the received vibration information to a collection unit configured to convert the vibration information from each of the vibrometers into a frequency domain to generate a frequency response, and extracting a second feature measured amount from the generated frequency response;

calculate a second difference between the extracted second feature measured amount and the reference feature amount; estimate a measured growth amount of the plurality of portions of the target plant by referencing the growth model, selecting a first difference, among the plurality of first modeled differences of each of the growth states, that is similar to the extracted second measured difference, acquiring a growth amount associated with the selected first modeled difference, wherein each of the reference feature amount, the first feature modeled amount, and the second feature measured amount have at least a resonance frequency and a Q value representing a sharpness of the resonance frequency; and iteratively monitoring and output growth information for each of the plurality of portions of the target plant and correlating at least two or more portions of growth information from two or more vibrometers to obtain a secondary growth state of the target plant.

4. The plant monitoring apparatus according to claim 3, wherein the each of the plurality of portions is a stem, a branch, or a leaf of the plant.

5. A non-transitory computer readable recording medium that includes a program recorded thereon, the program including instructions that causes a computer to carry out: executing a growth model simulation on a target plant to generate a growth model with respect to a plurality of portions of the target plant by:
  i) modeling a target plant to generate a plurality of plant models with respect to respective one or more states of the plurality of portions,
  ii) virtually applying vibration to the plant models to generate vibration information of each of the plant models in a time domain,
  iii) converting the vibration information into a frequency domain to generate a frequency response per plant model,
  iv) calculating a first feature modeled amount per plant model based on the generated frequency response,
  v) calculating a first difference, per plant model, between the first feature modeled amount of the plant model and a reference feature amount, and
  vi) generating a first growth model for each plant model by associating information for identifying a growth state of the plurality of portions corresponding to said plant model, a plurality of growth amounts of each identified growth state of the plurality of portions, and the calculated first differences corresponding to the plurality of growth amounts, the reference feature amount being a feature amount in a growth reference state of the target plant;

directly measured from the plurality of portion of the target plant, acquiring vibration information in a time domain, which has been generated by a plurality of vibrometers configured to apply vibration to each of the plurality of portions of the target plant and configured to receive the vibration information from each of the plurality of portions of the target plant, each of the vibrometers further configured to transmit the received vibration information to a collection unit configured to convert the vibration information from each of the vibrometers into a frequency domain to generate a frequency response, and extracting a second feature measured amount from the generated frequency response;

calculating a second difference between the extracted second feature measured amount and the reference feature amount; estimating a measured growth amount of the plurality of portions of the target plant by referencing the growth model, selecting a first difference, among the plurality of first modeled differences of each of the growth states, that is similar to the extracted second measured difference, acquiring a growth amount associated with the selected first modeled difference, wherein each of the reference feature amount, the first feature modeled amount, and the second feature measured amount have at least a resonance frequency and a Q value representing a sharpness of the resonance frequency; and iteratively monitoring and outputting growth information for each of the plurality of portions of the target plant and correlating at least two or more portions of growth information from two or more vibrometers to obtain a secondary growth state of the target plant.

6. The non-transitory computer readable recording medium according to claim 5, wherein the each of the plurality of portions is a stem, a branch, or a leaf of the plant.

* * * * *